(12) United States Patent
Bingham et al.

(10) Patent No.: US 11,739,600 B2
(45) Date of Patent: Aug. 29, 2023

(54) DEGASSING AND ANALYZING DRILLING FLUID

(71) Applicant: M-I L.L.C., Houston, TX (US)

(72) Inventors: Richard Bingham, Katy, TX (US); Reda Karoum, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 776 days.

(21) Appl. No.: 16/639,583

(22) PCT Filed: Aug. 28, 2018

(86) PCT No.: PCT/US2018/048216
§ 371 (c)(1),
(2) Date: Feb. 16, 2020

(87) PCT Pub. No.: WO2019/060098
PCT Pub. Date: Mar. 28, 2019

(65) Prior Publication Data
US 2021/0131203 A1 May 6, 2021

Related U.S. Application Data

(60) Provisional application No. 62/560,662, filed on Sep. 19, 2017.

(51) Int. Cl.
*E21B 21/06* (2006.01)
*B01D 19/00* (2006.01)
(Continued)

(52) U.S. Cl.
CPC ........ *E21B 21/067* (2013.01); *B01D 19/0036* (2013.01); *B01D 19/0042* (2013.01);
(Continued)

(58) Field of Classification Search
None
See application file for complete search history.

(56) References Cited

U.S. PATENT DOCUMENTS 3,469,617 A 9/1969 Palmason
3,895,927 A 7/1975 Bournham, Sr.
(Continued)

FOREIGN PATENT DOCUMENTS

EP 3032026 A1 6/2016
RU 2569427 C1 11/2015
(Continued)

OTHER PUBLICATIONS

Extended Search Report of European Patent Application No. 18857987.4 dated Apr. 28, 2021, 8 pages.
(Continued)

*Primary Examiner* — Christopher P Jones
*Assistant Examiner* — Phillip Y Shao
(74) *Attorney, Agent, or Firm* — Jeffrey D. Frantz

(57) ABSTRACT

Apparatus and methods for degassing and analyzing drilling fluid discharged from a wellbore at an oil and gas wellsite. The apparatus may be a drilling fluid analysis system having a gas analyzer, a fluid analyzer, and a degasser operable to release and separate mud gas entrained in the drilling fluid. The degasser may include a gas-liquid separator having a separator inlet configured to receive the drilling fluid containing the entrained mud gas, a first separator outlet for discharging the mud gas fluidly connected with the gas analyzer, and a second separator outlet for discharging degassed drilling fluid fluidly connected with the fluid analyzer.

18 Claims, 6 Drawing Sheets

(51) Int. Cl.
 *B01D 33/03* (2006.01)
 *B01D 33/41* (2006.01)
 *G01N 33/28* (2006.01)

(52) U.S. Cl.
 CPC ..... *B01D 19/0063* (2013.01); *B01D 33/0346* (2013.01); *B01D 33/41* (2013.01); *E21B 21/065* (2013.01); *G01N 33/2823* (2013.01)

(56) References Cited

U.S. PATENT DOCUMENTS

| | | | |
|---|---|---|---|
| 5,510,017 A | | 4/1996 | Abdullayev |
| 6,004,024 A | * | 12/1999 | Ho ................... B01F 25/31243 523/319 |
| 2003/0183585 A1 | | 10/2003 | Cho |
| 2004/0208801 A1 | | 10/2004 | Huziwara et al. |
| 2004/0265176 A1 | | 12/2004 | Kerherve et al. |
| 2006/0054510 A1 | | 3/2006 | Salerno |
| 2007/0006640 A1 | | 1/2007 | Gysling |
| 2008/0190668 A1 | * | 8/2008 | Swartout ................. F23G 7/085 175/207 |
| 2009/0139345 A1 | | 6/2009 | Xie |
| 2011/0245112 A1 | | 10/2011 | Harvey et al. |
| 2015/0267523 A1 | | 9/2015 | Saponja et al. |
| 2016/0263523 A1 | | 9/2016 | Van Dyke et al. |

FOREIGN PATENT DOCUMENTS

| | | |
|---|---|---|
| WO | 2001072432 A1 | 10/2001 |
| WO | 2004/080565 A1 | 9/2004 |
| WO | 2005119001 A1 | 12/2005 |
| WO | 2016076825 A1 | 5/2016 |

OTHER PUBLICATIONS

International Preliminary Report on Patentability for the International patent application PCT/US2018/048216 dated Apr. 2, 2020.
International Search Report and Written Opinion for the International patent application PCT/US2018/048216 dated Dec. 17, 2018.
Office Action issued inColombia Patent Application No. NC2020/0004166 dated Nov. 24, 2022, 30 pages with English translation.
Intent to Grant issued in European Patent Application 18857987.4 dated Nov. 21, 2022, 8 pages.
Office Action issued in Colombia Patent Application No. NC2020/0004166 dated Apr. 13, 2023, 28 pages with English translation.

* cited by examiner

DEGASSING AND ANALYZING DRILLING FLUID

CROSS-REFERENCE TO RELATED APPLICATIONS

This application claims priority to and the benefit of U.S. Provisional Application No. 62/560,662, titled "DEGASSER," filed Sep. 19, 2017, the entire disclosure of which is hereby incorporated herein by reference.

BACKGROUND OF THE DISCLOSURE

Wells are generally drilled into the ground or ocean bed to recover natural deposits of oil and gas, as well as other desirable materials that are trapped in subterranean formations. Such wells are drilled into the formations using a drill bit attached to the lower end of a drill string. Drilling fluid is pumped from the wellsite surface down through the drill string to the drill bit. The drilling fluid lubricates and cools the bit, and carries drill cuttings from the wellbore to the wellsite surface.

During the drilling operations, hydrocarbons, including gases from the subterranean formation (i.e., formation gases), become entrained or otherwise mix with the drilling fluid before returning to the wellsite surface. Formation fluid or gas logging is the practice of removing a portion of those hydrocarbons from the drilling fluid and measuring their composition and concentration. This practice can provide human wellsite operators with first measurement of the hydrocarbons present in the subterranean formation, which may be utilized to determine reservoir properties, such as architecture, connectivity, and compositional gradients. Mud gas logging may also inform the wellsite operators of the presence and/or levels of hazardous gases in the subterranean formation. Mud gas logging (i.e., mud gas logging) may be performed via surface gas sensors, such as gas detectors and gas chromatography analyzers. Although mud gases may be indicative of hydrocarbons present in the subterranean formation, the presence of such gases within the drilling fluid can interfere with or inhibit accurate measurements of composition, properties, and/or characteristics of the drilling fluid discharged from the wellbore. Thus, before the mud gas logging may be performed, the mud gases should be extracted in a controlled manner or otherwise separated from the drilling fluid at the wellsite surface. Mud gas logging is typically performed by manually operated devices that induce mechanical agitation to extract or separate the mud gases from the drilling fluid. Such devices are installed in association with various solids control equipment at different locations of the wellsite and operated manually by the wellsite operators, rendering gas measurements inconsistent and/or inaccurate.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces an apparatus including a degasser to release and separate mud gas entrained in drilling fluid discharged from a wellbore at an oil and gas wellsite. The degasser includes a gas-liquid separator and a venturi ejector. The gas-liquid separator includes a separator inlet to receive the drilling fluid containing the entrained mud gas, a first separator outlet to discharge the mud gas, and a second separator outlet to discharge degassed drilling fluid. The venturi ejector moves the drilling fluid containing the entrained mud gas from a drilling fluid source to the gas-liquid separator. The venturi ejector includes a first ejector inlet to fluidly connect with a motive gas source, a second ejector inlet to fluidly connect with the drilling fluid source, and an ejector outlet fluidly connected with the separator inlet.

The present disclosure also introduces an apparatus including a drilling fluid analysis system that includes a gas analyzer, a fluid analyzer, and a degasser. The degasser releases and separates mud gas entrained in drilling fluid discharged from a wellbore at an oil and gas wellsite. The degasser includes a gas-liquid separator that includes a separator inlet to receive the drilling fluid containing the entrained mud gas, a first separator outlet for discharging the mud gas fluidly connected with the gas analyzer, and a second separator outlet for discharging degassed drilling fluid fluidly connected with the fluid analyzer.

The present disclosure also introduces an apparatus including a shale shaker to remove solid particles from drilling fluid discharged from a wellbore at an oil and gas wellsite. The shale shaker includes a header box to receive the drilling fluid, a basket, a screen disposed within the basket, and a degasser. The degasser releases and separates mud gas entrained in the drilling fluid received into the header box. The degasser includes a gas-liquid separator having a separator inlet to receive the drilling fluid containing the entrained mud gas, a first separator outlet to discharge the mud gas, and a second separator outlet to discharge degassed drilling fluid. The degasser also includes a venturi ejector to move the drilling fluid from the header box to the gas-liquid separator. The venturi ejector includes a first ejector inlet to fluidly connect with a motive gas source, a second ejector inlet fluidly connected with the header box, and an ejector outlet fluidly connected with the separator inlet.

The present disclosure also introduces a method including performing drilling operations to form a wellbore at an oil and gas wellsite and operating a degasser at the oil and gas wellsite to release and separate mud gas entrained in drilling fluid discharged from the wellbore. The method also includes operating a gas analyzer to analyze the mud gas discharged from the degasser, and operating a fluid analyzer to analyze degassed drilling fluid discharged from the degasser.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
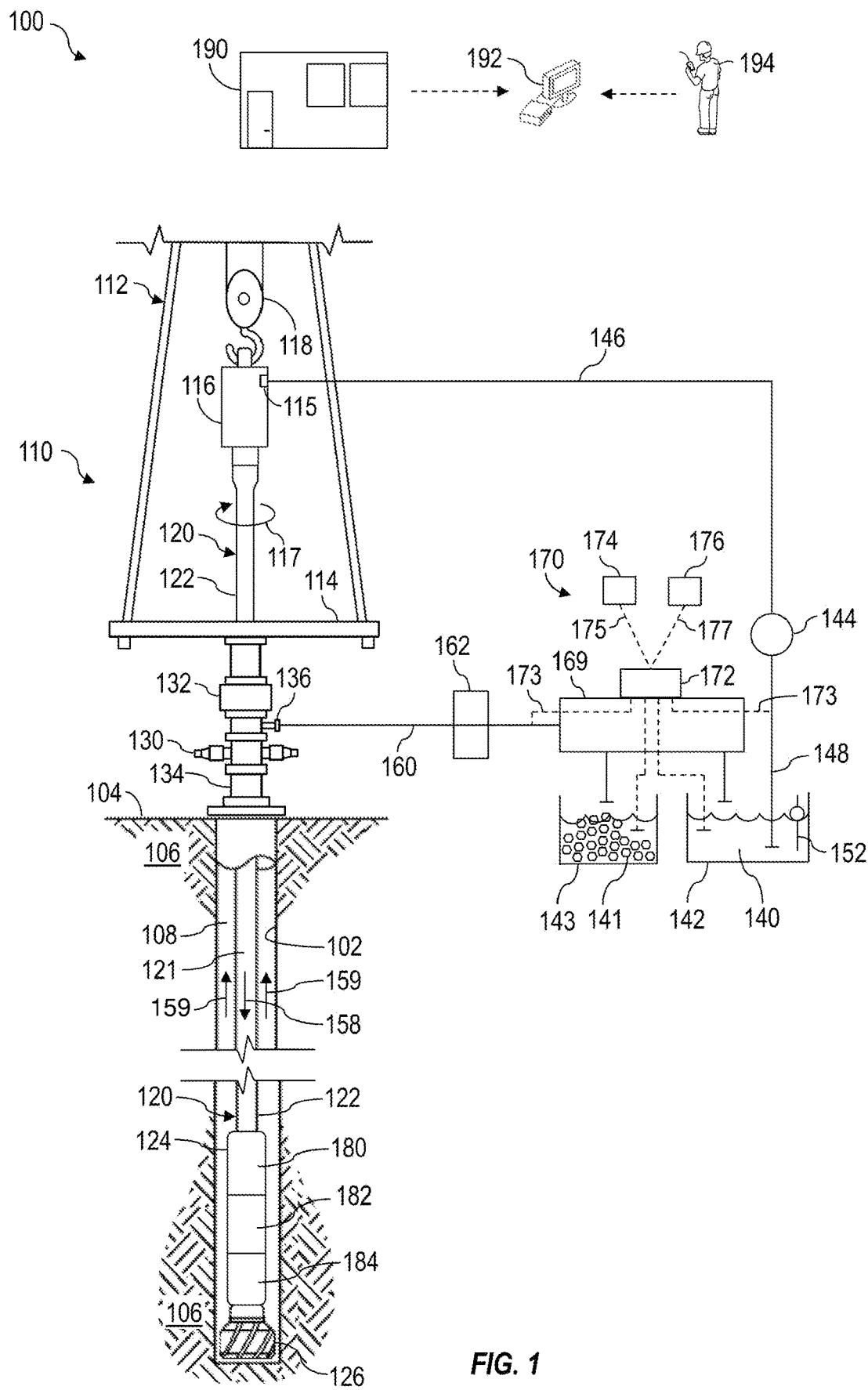
FIG. 1 is a schematic view of at least a portion of an example implementation of apparatus according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity, and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1 is a schematic view of at least a portion of an example implementation of a wellsite system 100 according to one or more aspects of the present disclosure. The wellsite system 100 represents an example environment in which one or more aspects described below may be implemented. It is also noted that although the wellsite system 100 is depicted as an onshore implementation, it is understood that the aspects described below are also generally applicable to offshore implementations.

The wellsite system 100 is depicted in relation to a wellbore 102 formed by rotary and/or directional drilling from a wellsite surface 104 and extending into a subterranean formation 106. The wellsite system 100 comprises surface equipment 110 located at the wellsite surface 104, including a platform, rig, derrick, and/or other wellsite structure 112 having a rig floor 114 positioned over the wellbore 102. A drill string 120 suspended within the wellbore 102 from the wellsite structure 112 comprises a bottom hole assembly (BHA) 124 and means 122 for conveying the BHA 124 within the wellbore 102. The conveyance means 122 may comprise drill pipe, heavyweight drill pipe (HWDP), wired drill pipe (WDP), tough logging condition (TLC) pipe, coiled tubing, and/or other means of conveying the BHA 124 within the wellbore 102.

The BHA 124 connected at the lower end of the conveyance means 122 may be coupled to a drill bit 126 and may include various downhole tools 180, 182, 184. One or more of such downhole tools 180, 182, 184 may be or comprise an acoustic tool, a density tool, a directional drilling tool, an electromagnetic (EM) tool, a sampling while drilling (SWD) tool, a formation testing tool, a formation sampling tool, a gravity tool, a monitoring tool, a neutron tool, a nuclear tool, a photoelectric factor tool, a porosity tool, a reservoir characterization tool, a resistivity tool, a seismic tool, a surveying tool, and/or a tough logging condition (TLC) tool, although other downhole tools are also within the scope of the present disclosure. One or more of the downhole tools 180, 182, 184 may also be implemented as a measuring-while-drilling (MWD) or logging-while-drilling (LWD) tool for the acquisition and/or transmission of downhole data to the surface equipment 110.

Rotation of the drill bit 126 and the weight of the drill string 120 may operate to advance the BHA 124 into the formation 106 to form the wellbore 102. The drill bit 126 may be rotated from the wellsite surface 104 and/or via a downhole mud motor (not shown) connected with the drill bit 126. To facilitate rotation of the drill bit 126 from the wellsite surface 104, the wellsite structure 112 may comprise a top drive 116 connected to the uphole end of the conveyance means 122 in a manner permitting rotary motion 117 to be imparted to the drill string 120. The top drive 116 (and, thus, the drill string 120) may be suspended from the wellsite structure 112 via a travelling block 118 and a drawworks (not shown) or another tensioning device operable to selectively move the top drive 116 and the drill string 120 in uphole and downhole directions during drilling operations. However, a kelly and rotary table may be utilized instead of or in addition to the top drive 116.

The drill string 120 may be conveyed into the wellbore 102 through a plurality of well control devices disposed at the wellsite surface 104 on top of the wellbore 102 below the rig floor 114. The well control devices may include a blowout preventer (BOP) stack 130 and an annular fluid control device 132, such as an annular preventer and/or a rotating control device (RCD). The well control devices may be mounted on top of a wellhead 134.

The wellsite system 100 is operable to circulate fluids between the surface equipment 110 and downhole portions of the drill string 120 during drilling and other operations. For example, the wellsite system 100 may be operable to inject drilling fluid from the wellsite surface 104 into the wellbore 102 via an internal fluid passage 121 extending longitudinally through the drill string 120. Such wellsite system 100 may comprise a pit, a tank, and/or other fluid container 142 (e.g., an active pit) holding drilling fluid 140, and a pump 144 operable to move the drilling fluid 140 from the container 142 to a fluid inlet 115 of the top drive 116 via a fluid conduit 146 extending between the pump 144 and the top drive 116. The pump 144 and the container 142 may be fluidly connected by a fluid conduit 148.

During drilling operations, the drilling fluid may be pumped through an internal flow pathway (not shown) of the top drive 116 and into the internal passage 121 of the drill string 120. The drilling fluid 140 may continue to flow downhole through the conveyance means 122 and the BHA 124, as indicated by directional arrow 158. The drilling fluid may exit the BHA 124 via ports in the drill bit 126 and then circulate uphole through an annular space ("annulus") 108 of the wellbore 102 defined between an exterior of the drill string 120 and the wall of the wellbore 102, as indicated by directional arrows 159. In this manner, the drilling fluid lubricates the drill bit 126 and carries formation cuttings uphole to the wellsite surface 104. The drilling fluid may exit the annulus 108 via a spool a wing valve, a bell nipple, or another adapter 136 permitting ported access or fluid connection with the annulus 108.

The drilling fluid exiting the annulus 108 via the adapter 136 may be directed into a fluid conduit 160 and pass through various pieces of surface equipment 110 fluidly connected along the conduit 160, prior to being returned to the container 142 to be recirculated into the wellbore 102. For example, the drilling fluid may pass through a choke manifold 162 connected along the conduit 160. The choke manifold 162 may include at least one choke and a plurality of fluid control valves (neither one shown) collectively operable to control flow of the drilling fluid through the choke manifold 162.

Before being returned to the container 142, the drilling fluid returning to the wellsite surface 104 may be cleaned and/or reconditioned via drilling fluid reconditioning equipment 169, which may include one or more of liquid gas separators (e.g., poor boy separators), shale shakers, centrifuges, and other drilling fluid cleaning, reconditioning, and/or other processing equipment. The liquid gas separators may remove mud gases entrained in the drilling fluid discharged from the wellbore 102 and the shale shakers may separate and remove solid particles 141 (e.g., drill cuttings) from the drilling fluid into a solids container 143 (e.g., a reserve pit). The drilling fluid reconditioning equipment 169 may further comprise equipment operable to remove gas and finer formation cuttings from the drilling fluid and/or modify physical properties (e.g., rheology) of the drilling fluid. For example, the drilling fluid reconditioning equipment 169 may include a process degasser, desander, desilter, mud cleaner, and/or decanter, among other examples. Such equipment may be or comprise industrial or large scale process equipment fluidly connected with the fluid conduit 160, such as may be operable to pass, recondition, and/or otherwise process large flow rates (e.g., more than 100 gallon per minute (GPM)) of drilling fluid. A plurality of intermediate tanks or containers (not shown) may be utilized to hold the drilling fluid as the drilling fluid progresses through the various portions or stages of the drilling fluid reconditioning equipment 169.

The wellsite system 100 may further comprise one or more drilling fluid analysis systems 170 (e.g., testing instruments) for testing or otherwise analyzing the drilling fluid discharged from the wellbore 102. The analysis systems 170 may be fluidly connected with or along the fluid conduit 160, the drilling fluid reconditioning equipment 169, the drilling fluid container 142, and/or the fluid conduit 148, which may be individually or collectively referred to as a "drilling fluid source." The analysis systems 170 may be or comprise one or more test instruments operable to extract or otherwise receive some (e.g., a sample) of the drilling fluid, a constituent of the drilling fluid, and/or a substance carried by the drilling fluid from the drilling fluid source for analysis. Each analysis system 170 may comprise a degasser 172, which may be fluidly connected in association with one or more portions of the drilling fluid source. The degasser 172 may be operable to receive the drilling fluid passing through or contained within the drilling fluid source and release and/or separate gases entrained within the drilling fluid. The degasser 172 may be fluidly connected with a gas analyzer 174 via a fluid conduit 175, such as may permit formation and other gases separated and/or released by the degasser 172 to be directed to and analyzed by the gas analyzer 174. The gas analyzer 174 may comprise one or more fluid detectors, sensors, and/or analyzers, each operable to generate signals or information indicative of presence and/or quantity of formation and other gases contained within the drilling fluid discharged from the wellbore 102. The gas analyzer 174 may be or comprise qualitative gas analyzers, which may be utilized for safety purposes, such as to detect presence of hazardous gases entrained within the returning drilling fluid. The gas analyzer 174 may also or instead be or comprise quantitative gas analyzers, which may be utilized to detect levels or relative quantities of gases, such as to perform formation evaluation. The degasser 172 may also or instead be fluidly connected with a fluid analyzer 176 (e.g., liquidized or liquid fluid analyzer) via a fluid conduit 177, such as may permit degassed drilling fluid discharged from the degasser 172 to be directed to and analyzed by the fluid analyzer 176. The fluid analyzer 176 may comprise one or more gas detectors, sensors, and/or analyzers, each operable to generate signals or information indicative of components, properties, and/or characteristics of the drilling fluid discharged from the wellbore 102. Example implementations of the analyzers 174, 176 are described below.

The degasser 172 may be adapted to release and/or separate entrained gases, such as residual formation and other gases that are enriched in heavier isotopes, from the drilling fluid. The degasser 172 may be utilized to release and/or separate the entrained gases from drilling fluid that is newly discharged from the wellbore 102, prior to being reconditioned or otherwise processed by the drilling fluid reconditioning equipment 169. For example, the degasser 172 may be fluidly connected with or along the fluid conduit 160 between the choke manifold 162 and the drilling fluid reconditioning equipment 169, or otherwise upstream from the drilling fluid reconditioning equipment 169, such as may permit the degasser 172 to release and/or separate the entrained mud gases in the drilling fluid before or while the drilling fluid enters the drilling fluid reconditioning equipment 169. The degasser 172 may also or instead be fluidly connected with the liquid gas separator (i.e., poor boy) or a header box of a shale shaker (such as the shale shaker 400 shown in FIG. 4), such as may permit the degasser 172 to receive the drilling fluid located within the header box. The degasser 172 of another drilling fluid analysis system 170 may also or instead be utilized to release and/or separate entrained gases from drilling fluid that has been received, reconditioned, and/or discharged by the drilling fluid reconditioning equipment 169. The degasser 172 may, thus, be fluidly connected, for example, with the fluid conduit 160, the solids container 143, the fluid container 142, the fluid conduit 148 via corresponding fluid conduits 173, and/or another intermediate container or conduit of the drilling fluid reconditioning equipment 169 such as may permit mud gases to be monitored at different locations.

The surface equipment 110 of the wellsite system 100 may also comprise a control center 190 from which various portions of the wellsite system 100 may be monitored and controlled. The control center 190 may be located on the rig floor 114 or another location at the wellsite surface 104. The control center 190 may contain a control workstation 192 (e.g., a computer, a control panel) operable to provide monitoring and operational control of one or more portions of the wellsite system 100, including the surface equipment 110 and the drill string 120. For example, the control workstation 192 may be communicatively connected with the various surface and downhole equipment describe herein and operable to receive signals or information from and transmit control signals to such equipment to perform various operations described herein. The control workstation 192 may include an input device for receiving commands from a human wellsite operator 194 and an output device for displaying information to the wellsite operator 194. The control workstation 192 may comprise a processing device (e.g., processing device 600 shown in FIG. 6) operable to receive, store, and process executable programs and/or instructions, including for implementing one or more aspects of methods and/or operations described herein. Communication between the control center 190, the control workstation 192, and the various wellsite equipment may be via wired and/or wireless communication means. However, for clarity and ease of understanding, such communication means are not depicted, and a person having ordinary skill in the art will appreciate that such communication means are within the scope of the present disclosure.

The signals or information generated by the gas and fluid analyzers 174, 176 may be received and processed in real time by the control workstation 192 or another processing device (e.g., processing device 600 shown in FIG. 6), such as to monitor composition, properties, and/or characteristics of the drilling fluid discharged from the wellbore 102, which, in turn, may be indicative of hydrocarbon reservoir properties. Monitoring the drilling fluid before and after the drilling fluid is reconditioned or otherwise processed by the drilling fluid reconditioning equipment 169 may permit the processing device to account for gases and/or fluids that remain within the drilling fluid while it circulates through the drill string 120, the wellbore 102, and the surface equipment 110. Differentiating between drilling fluid measurements taken before and after processing by the drilling fluid reconditioning equipment 169 may facilitate measurements of "new" (background) gas and/or fluid that were introduced into the drilling fluid during the most recent pass through the wellbore 102. The background gas may include gas generated by the mud and recycled gas. Background gas measurements may be subtracted from current mud gas measurements (e.g., at the shale shaker) to obtain formation gas measurements. When the background gas measurements are subtracted, the mud gas measurements then become or are indicative of the formation gas measurements. Drilling fluid measurements taken before and/or after processing by the drilling fluid reconditioning equipment 169 may also be utilized to control the drilling fluid reconditioning equipment 169 or other mud control equipment of the wellsite system 100 to change the composition, properties, and/or characteristics of the drilling fluid before it is injected back into the wellbore 102.

Figure 2:
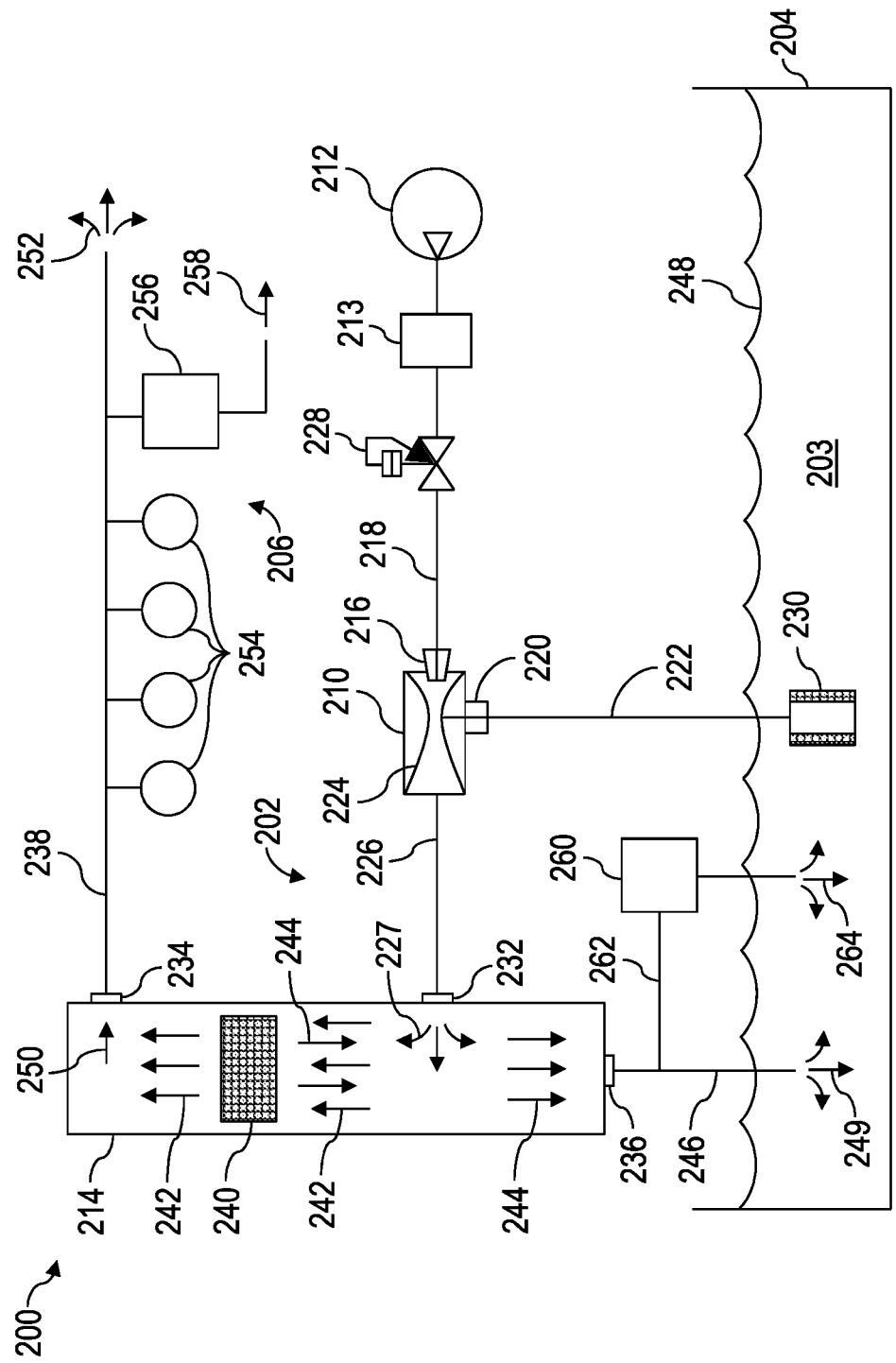
FIG. 2 is a schematic view of at least a portion of an example implementation of apparatus according to one or more aspects of the present disclosure.

FIG. 2 is a schematic view of at least a portion of an example implementation of a drilling fluid analysis system 200 according to one or more aspects of the present disclosure. The analysis system 200 may comprise a degasser 202 (i.e., a degassing system) fluidly or otherwise operatively connected with a source 204 of drilling fluid 203 and with gas and/or fluid analyzers 206, 260. The analysis system 200 may comprise one or more features of the analysis system 170 shown in FIG. 1, except as described below. The following description refers to FIGS. 1 and 2, collectively.

The degasser 202 may be operable to release and/or separate formation and other gases entrained in the drilling fluid 203 discharged from the annulus 108 of the wellbore 102 and passing through or otherwise contained within the drilling fluid source 204. The source 204 may be or comprise, for example, the fluid conduit 160, the drilling fluid reconditioning equipment 169, the drilling fluid container 142, and/or the fluid conduit 148. The degasser 202 may comprise a venturi ejector 210 fluidly connected with a gas-liquid separator 214, the drilling fluid source 204, and a source 212 of pressurized motive gas (e.g., air, nitrogen, etc.). The venturi ejector 210 may be or comprise an eductor, which may be operable to move the drilling fluid 203 from the drilling fluid source 204 to the gas-liquid separator 214. The venturi ejector 210 may comprise a nozzle 216 (i.e., a first ejector inlet) operable to receive the motive gas from the motive gas source 212 via a fluid conduit 218. The venturi ejector 210 may further comprise a suction port 220 (i.e., a second ejector inlet) operable to receive the drilling fluid from the source 204 via a fluid conduit 222. The venturi ejector 210 may further comprise a diffuser 224 (i.e., an ejector outlet) operable to discharge the drilling fluid received from the source 204 into the gas-liquid separator 214 via a fluid conduit 226. The nozzle 216 may have an adjustable insertion distance into or otherwise with respect to the diffuser 224.

The motive gas source 212 may be or comprise a gas compressor, such as an air compressor operable to capture and pressurize ambient air, and selectively transfer the pressurized air into and through the venturi ejector 210. The motive gas source 212 may instead be or comprise a nitrogen converter unit or generator operable to compress and separate air captured from the ambient atmosphere to provide pressurized nitrogen gas, which may be compressed by the gas compressor and/or selectively transferred into and through the venturi ejector 210. The motive gas discharged from the motive gas source 212 may be cleaned to remove hydrocarbons and utilized as a vector gas (baseline) to measure hydrocarbon concentrations originating from the drilling fluid 203. A gas cleaning device 213 (e.g., a catalytic converter) may be connected between the motive gas source 212 and the venturi ejector 210 to remove hydrocarbons (e.g., oil) and/or other contaminants from the pressurized motive gas, such as via adsorption and/or another chemical process.

During operations, the nozzle 216 may increase the velocity of the motive gas received from the gas source 212, forming a gas jet, which may be directed into and through the diffuser 224, resulting in generation of vacuum (i.e., suction) at the suction port 220. The vacuum may be applied to the source 204 via the conduit 222 to draw the drilling fluid 203 from the source 204 into the venturi ejector 210. When the drilling fluid 203 reaches the diffuser 224, the gas jet may push the drilling fluid 203 out of the venturi ejector 210 via the diffuser 224 and into the gas-liquid separator 214 via the conduit 226, as indicated by arrows 227. The venturi ejector 210 may accelerate the drilling fluid and motive gas mixture to a high velocity through the diffuser 224 of the venturi ejector 210. As the mixture exits the diffuser 224, the mixture expands back to downstream line pressure conditions, which may be at atmospheric pressure. Expansion and acceleration may create an environment that induces atomization of the drilling fluid 203, such as may facilitate gases entrained in the drilling fluid 203 to separate from the liquid drilling fluid 203. Such expansion and acceleration may also or instead agitate the drilling fluid 203 and increase surface area of the drilling fluid 203, which can collectively cause the gases entrained in the drilling fluid 203 to be released.

A pressure control valve 228 (e.g., a pressure regulator) may be fluidly connected along the conduit 218 for controlling flow rate of the motive gas flowing into and through the venturi ejector 210. Pressure setting may be selected to cause a predetermined motive gas flow rate and jet velocity through the venturi ejector 210, which, in turn, may cause a predetermined level or amount of vacuum generated by the venturi ejector 210 to cause a predetermined flow rate of the drilling fluid 203 to be drawn from the source 204 and discharged into the gas-liquid separator 214. The pressure setting may be set to a constant value, which may result in a substantially constant flow rate of the drilling fluid 203 to be drawn from the source 204. Orifice size of the nozzle 216 and pressure of the motive gas may be utilized to determine actual flow rate of the motive gas passing through the venturi ejector 210.

The fluid conduit 222 may terminate with a suction strainer 230 or another filter disposed within the source 204 and submerged within the drilling fluid 203. The suction strainer 230 may be operable to prevent or inhibit solid particles suspended in the drilling fluid 203 from being drawn into the venturi ejector 210 via the conduit 222. For example, the suction strainer 230 may comprise a 1.00 millimeter (mm) opening aperture size.

The gas-liquid separator 214 may be operable to separate gases, including the released mud gases and the motive gas, from the liquid (including suspended solids) portion of the drilling fluid 203. The gas-liquid separator 214 may be or comprise a fluid separation column or vessel comprising a fluid inlet 232 fluidly connected with the conduit 226, a gas outlet 234 fluidly connected with the gas analyzer 206 (e.g., a gas analysis module or system) via a conduit 238, and a liquid (i.e., degassed fluid) outlet 236 fluidly connected with the source 204 or another drilling fluid destination. The gas-liquid separator 214 may comprise a demister 240 disposed between the inlet 232 and the outlet 234. The demister 240 may be operable to coalesce or aggregate the airborne particles of the drilling fluid passing through the gas-liquid separator 214 from the inlet 232 to the outlet 234, as indicated by arrows 242, until such airborne particles adhere to the demister 240 and/or become heavy enough to fall downwards, as indicated by arrows 244, toward the bottom of the gas-liquid separator 214. The demister 240 may comprise one or more mesh screens, filters, vanes, baffles, or another structure operable to coalesce the airborne drilling fluid particles or droplets. The drilling fluid 203 particles may settle or collect at the bottom of the gas-liquid separator 214 or the drilling fluid 203 may be drained into the source 204 or another drilling fluid destination via the liquid outlet 236. The settled drilling fluid 203 that is discharged from the gas-liquid separator 214 via the outlet 236 may be referred to hereinafter as "degassed drilling fluid."

The liquid outlet 236 may be fluidly connected with the source 204 or another destination via a fluid conduit 246 or the gas-liquid separator 214 may be partially disposed within the source 204 or another destination such that the liquid outlet 236 is located within the source 204 or another destination, thereby permitting the drilling fluid 203 to be discharged into the source 204 or another destination, as indicated by arrows 249. The end of the conduit 246 or the liquid outlet 236 may be submerged beneath a surface 248 of the drilling fluid 203, such as may expose the end of the conduit 246 or the liquid outlet 236 to hydrostatic pressure of the drilling fluid 203. The hydrostatic pressure may form a fluid seal, such as may prevent or inhibit positive pressure within the gas-liquid separator 214 from causing the airborne drilling fluid and gases injected into the gas-liquid separator 214 to flow out of the gas-liquid separator 214 via the liquid outlet 236 and fluid conduit 246. The hydrostatic pressure at the liquid outlet 236 and/or the fluid conduit 246 may cause the airborne drilling fluid and the gases to flow upwardly through the demister 240, thereby causing the airborne drilling fluid to coalesce and the gases to pass through the demister 240 and out of the gas-liquid separator 214 via the gas outlet 234, as indicated by arrow 250. The end of the conduit 246 or the liquid outlet 236 may be submerged about one inch or more below the surface 248 of the drilling fluid 203.

At least a portion of the degassed drilling fluid discharged from the gas-liquid separator 214 may be analyzed by the fluid analyzer 260 (e.g., a fluid analysis module or system) fluidly connected with the gas-fluid separator 214. The fluid analyzer 260 may be operable to receive the degassed drilling fluid and monitor or otherwise detect various properties and characteristics of the drilling fluid 203 discharged from the wellbore 102. For example, the fluid analyzer 260 may be or comprise a qualitative fluid analyzer operable to detect, for example, physical and/or chemical properties of the drilling fluid 203. The fluid analyzer 260 may also or instead be or comprise a quantitative fluid analyzer operable to detect, for example, composition or relative quantities of individual fluids making up the drilling fluid 203. Analyzing the drilling fluid that has been degassed may facilitate more accurate measurements and/or analysis, which may be skewed or otherwise rendered inaccurate by presence of gases.

The fluid analyzer 260 may be fluidly connected with the fluid conduit 246 or otherwise with the gas-liquid separator 214 via a fluid conduit 262, such as may permit at least a portion of the degassed drilling fluid to be directed to and/or through the fluid analyzer 260 for analysis. The analyzed degassed drilling fluid may be expelled or discharged back into the source 204 or another destination, as indicated by arrows 264.

The fluid analyzer 260 may contain or otherwise comprise, for example, a nuclear magnetic resonance (NMR) analyzer, such as may be operable to detect composition and distribution of solids and fluids (e.g., oil, water) within the degassed drilling fluid. The NMR analyzer may be utilized, for example, to perform direct hydrocarbon typing and/or enhanced diffusion to identify individual components of the drilling fluid 203. The fluid analyzer 260 may also or instead contain or otherwise comprise a spectrometer operable to measure one or more optical characteristics of the degassed drilling fluid and output optical spectra and/or other data representative of the detected optical characteristics. The optical characteristics may include optical density of the drilling fluid 203 at each detected wavelength and/or wavelength range. Each wavelength or wavelength range may correspond to a compositional component of the drilling fluid 203. The fluid analyzer 260 may also or instead contain or otherwise comprise an electrical stability measurement device operable to measure emulsion strength and oil-wetting qualities of the drilling fluid 203, such as by applying an increasing voltage across an electrode gap of a probe immersed within a sample of the degassed drilling fluid. The fluid analyzer 260 may also or instead contain or otherwise comprise a rheology analyzer operable to receive a predetermined volume of the degassed drilling fluid and measure flow properties (e.g., viscosity, plastic viscosity (PV), yield point (YP), etc.) of the degassed drilling fluid, such as with respect to strain rate and/or temperature changes. The fluid analyzer 260 may also or instead contain or otherwise comprise one or more of a pH sensor, a salinity sensor, a density sensor, and a temperature sensor.

The various sensors and/or analyzers of the fluid analyzer 260 may be fluidly connected in series and/or in parallel, such as may permit simultaneous real time monitoring of composition, properties, and/or characteristics of the drilling fluid 203. One or more of the sensors and/or analyzers of the fluid analyzer 260 (e.g., the rheology analyzer) may periodically capture a predetermined volume or batch of the degassed drilling fluid, which may then be analyzed or tested for a predetermined period of time. Other sensors and/or analyzers of the fluid analyzer 260 (e.g., the pH sensor, the temperature sensor) may operate to instantaneously or promptly measure a property or characteristic of the drilling fluid via mere contact with passing drilling fluid 203 and, thus, may be mounded along or within a fluid conduit forming or extending through the fluid analyzer 260. Each of the various sensors, devices, and/or analyzers of the fluid analyzer 260 may be operable to generate signals or information indicative of the corresponding fluid properties and characteristics of the degassed drilling fluid. Each of the various sensors and/or devices of the fluid analyzer 260 may be communicatively connected with the control workstation 192 or another processing device, which may be operable to receive and process the signals or information according to the stored executable programs and/or instructions, such as may facilitate real time monitoring of the composition, properties, and characteristics of the drilling fluid 203 being discharged from the wellbore 102.

The gases released from the drilling fluid discharged from the gas-liquid separator 214 may be conveyed along the conduit 238 to a piece of surface equipment (e.g., flare stack) or vented into the ambient atmosphere, as indicated by arrows 252. The gases passing through the conduit 238 may be analyzed by the gas analyzer 206 operatively connected with or along the conduit 238. The gas analyzer 206 may comprise a plurality of gas detectors 254, each operable to detect the presence of an individual gas (e.g., $H_2$, $CO_2$, $H_2S$, $CH_4$, TG, etc.). The gas detectors 254 may be utilized for safety purposes, such as to detect hazardous gases. For example, the gas detectors 254 may be operable to generate signals or information indicative of the gas molecular compositions (e.g., methane, ethane, propane, and/or the like). The gas analyzer 206 may also or instead comprise a quantitative gas analyzer 256, which may be utilized for formation evaluation. The gas analyzer 256 may be or comprise a device and/or circuitry operable to generate signals or information indicative of composition or relative quantities of individual gases (e.g., $CH_4$, $C_2H_6$, $C_3H_8$, $nC_4H_{10}$, $iC_4H_{10}$, $nC_5H_{12}$, $iC_5H_{12}$, etc.). The gas analyzer 256 may be or comprise a device operable to generate signals or information indicative of ratios of isotopes (e.g., $^{13}C/^{12}C$ of methane) of one or more molecules of gas within the drilling fluid 203 at separate and/or distinct instances of time. For example, the gas analyzer 256 may be operable to measure isotopic concentrations used to obtain a ratio of the isotopic measurements. The gas analyzer 256 may be implemented, for example, as a gas chromatograph-isotope ratio mass spectrometer (GC-IRMS), a spectrophotometer or photoacoustic detector working on the Tunable Diode Laser Absorption Spectroscopy (TDLAS) principle or the Cavity Ring Down Spectroscopy (CRDS), and/or other technology operable to provide relative concentration of isotopes of gas species (e.g., $^{13}C$ and $^{12}C$ in $CH_4$, or $^{18}O$ and $^{16}O$ in $CO_2$, etc.). Portion of the gases passing through the conduit 238 may be captured by the gas analyzer 256, such as via a pitot tube 257 (shown in FIG. 3), metered through the analyzer 256, and vented into the ambient atmosphere, as indicated by arrow 258. The gas analyzer 206 may be communicatively connected with the control workstation 192 or another processing device, which may be operable to receive the signals or information generated by the gas analyzer 206 and process the signals or information according to the stored executable programs and/or instructions, such as may facilitate real time monitoring of types and/or quantities of gases within the drilling fluid 203 being discharged from the wellbore 102.

The composition, properties, and characteristics of the monitored drilling fluid 203 may depend on location of the drilling fluid source 204 from which monitoring system 200 draws the drilling fluid 203. For example, the analysis system 200 may be operable to monitor drilling fluid that was just discharged from the wellbore 102, such as flowing along the fluid conduit 160, or drilling fluid that was at least partially reconditioned, such as being transferred through the drilling fluid reconditioning equipment 169. Furthermore, monitoring the composition, properties, and characteristics of the drilling fluid at the same source(s) and/or location(s) facilitates repeatability and more consistent readings than if such monitoring was conducted at locations that changed with time or otherwise between measurements.

The signals or information generated by the individual sensors and/or analyzers of the gas and fluid analyzers 206, 260 may be received in real time by the control workstation 192 or another processing device for controlling mud systems or equipment (e.g., drilling fluid reconditioning equipment 169) of the wellsite system 100. The control workstation 192 may then automatically and in real time adjust or otherwise change operation of such mud systems or equipment based on the received signals or information to adjust or otherwise change composition, properties, and/or characteristics of the drilling fluid 203 that is pumped back into the wellbore 102 to be within predetermined corresponding value ranges, such as to optimize drilling efficiency. For example, if the density sensor indicates that the density of the drilling fluid has dropped below a predetermined value, one or more portions of the mud systems or equipment may automatically and in real time add a weighting agent (e.g., barite) to the drilling fluid while the drilling fluid is reconditioned to maintain density of the drilling fluid within a predetermined range.

Figure 3:
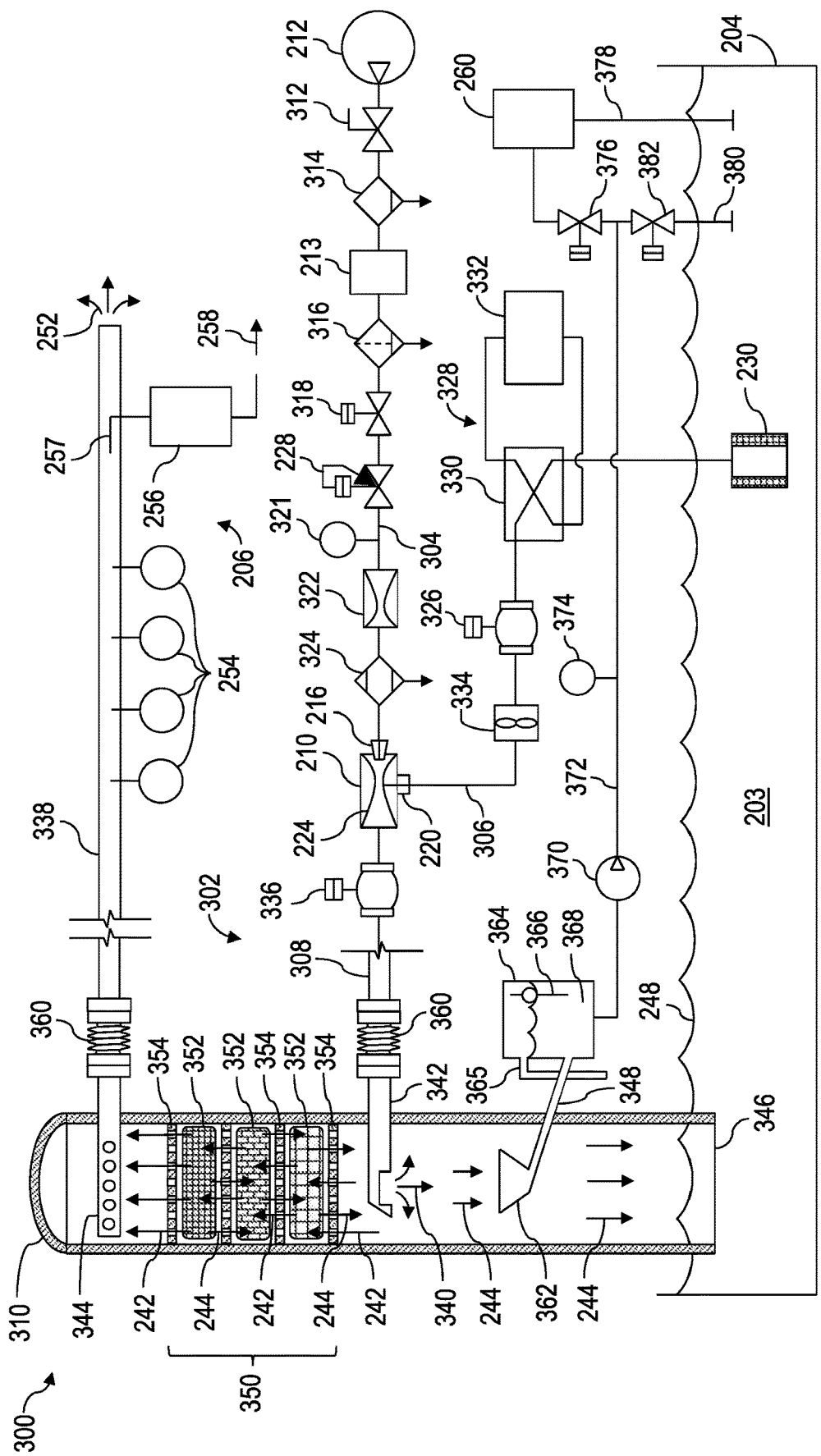
FIG. 3 is a schematic view of at least a portion of an example implementation of apparatus according to one or more aspects of the present disclosure.

FIG. 3 is a schematic view of at least a portion of an example implementation of a drilling fluid analysis system 300 according to one or more aspects of the present disclosure. The analysis system 300 may comprise a degasser 302 (i.e., a degassing system) fluidly or otherwise operatively connected with a source 204 of drilling fluid 203 and with gas and/or fluid analyzers 206, 260. The analysis system 300 may comprise one or more features of the analysis systems 170, 200 shown in FIGS. 1 and 2, respectively, including where indicated by like reference numbers, except as described below. The following description refers to FIGS. 1-3, collectively.

The degasser 302 may be operable to release and/or separate mud gases entrained in the drilling fluid 203 that is discharged from the annulus 108 of the wellbore 102 and passing through or otherwise contained within the drilling fluid source 204. The degasser 202 may comprise a venturi ejector 210 fluidly connected with a source 212 of pressurized motive gas (e.g., air, nitrogen, etc.) via a fluid conduit 304, with the drilling fluid source 204 via a fluid conduit 306 (i.e., a suction conduit), and with a gas-liquid separator 310 via a fluid conduit 308. The venturi ejector 210 may be or comprise an eductor, such as may be operable to move the drilling fluid 203 from the source 204 to the gas-liquid separator 310. The venturi ejector 210 may comprise a nozzle 216 (i.e., a first ejector inlet) operable to receive the motive gas from the motive gas source 212 via the fluid conduit 304, a suction port 220 (i.e., a second ejector inlet) operable to receive the drilling fluid from the source 204 via the fluid conduit 306, and a diffuser 224 (i.e., an ejector outlet) operable to discharge the drilling fluid 203 received from the source 204 into the gas-liquid separator 310 via the fluid conduit 308.

The motive gas discharged by the motive gas source 212 may be treated and controlled by a plurality of fluid treatment and control devices connected along the conduit 304. For example, a manual or a hand operated fluid control valve 312 maybe fluidly connected along the conduit 304 to selectively fluidly connect or disconnect the motive gas source 212 from the fluid conduit 304. The motive gas discharged from the motive gas source 212 may be cleaned to remove hydrocarbons and other contaminants, and utilized as a vector gas (baseline) to measure hydrocarbons originating from the drilling fluid 203. For example, a coalescer or another gas-liquid separator 314 maybe fluidly connected along the conduit 304 to dry or otherwise remove liquid mist or particles suspended within the motive gas flowing through the conduit 304. A filter 316 maybe fluidly connected along the conduit 304 to filter or otherwise remove contaminants (e.g., hydrocarbons) suspended within the motive gas flowing through the conduit 304. A gas cleaning device 213 (e.g., a catalytic converter) may be connected along the conduit 304 to remove hydrocarbons (e.g., oil) from the pressurized motive gas, such as via adsorption and/or another chemical process.

A remotely-operated fluid control valve 318 may be connected along the conduit 304 to selectively permit or prevent the motive gas from being introduced into the venturi ejector 210. The fluid control valve 318 may be actuated remotely by a corresponding actuator operatively coupled with the fluid control valve 318. A pressure control valve 228 and a fixed orifice valve 322 may be fluidly connected along the conduit 304 for collectively controlling the flow rate of the motive gas flowing into and through the venturi ejector 210. Pressure setting and size of the orifice valve 322 may be selected to cause a predetermined motive gas flow rate and jet velocity through the venturi ejector 210, which, in turn, may cause a predetermined level or amount of vacuum generated by the venturi ejector 210 to cause a predetermined flow rate of the drilling fluid 203 to be drawn from the source 204 and discharged into the gas-liquid separator 310. The pressure setting and size of the orifice valve 322 may be set to a constant value, which may result in a substantially constant flow rate of drilling fluid 203 to be drawn from the source 204. For example, the drilling fluid 203 may be drawn at a flow rate of about 350 milliliters per minute (0.092 gallons per minute). Because flow rates of both the motive gas and drilling fluid 203 are set to a known value, quantitative mud gas analysis may be performed by the control workstation 192 in conjunction with the gas analyzer 256.

A pressure sensor 321 may be connected along the fluid conduit 304 to measure pressure of the motive gas downstream from the pressure control valve 228. The pressure sensor 321 may be communicatively connected with the control workstation 192, such as may permit the control workstation 192 to receive the signals or information generated by the pressure sensor 321 and process the signals according to the executable programs and/or instructions stored in the control workstation 192. Orifice size of the nozzle 216 and pressure of the motive gas indicated by the pressure sensor 321 may be utilized to determine actual flow rate of the motive gas passing through the venturi ejector 210. A dryer 324 maybe fluidly connected along the conduit 304 to further dry or otherwise remove remaining moisture from the motive gas flowing through the conduit 304. The dryer 324 may be implemented as a desiccant dryer (e.g., regen or twin tower dryer), a refrigerated dryer, a deliquescent dryer, and a membrane dryer, among other examples.

The drilling fluid 203 drawn from the source 204 may be treated and/or controlled by a plurality of fluid treatment and control devices connected along the conduit 306. A remotely-operated fluid control valve 326 may be connected along the conduit 306 to selectively permit or prevent the drilling fluid from being drawn into the venturi ejector 210. The fluid control valve 326 may be actuated remotely by a corresponding actuator operatively coupled with the fluid control valve 326. A heater 328 may be connected along the conduit 306 for increasing the temperature of the drilling fluid 203 flowing through the conduit 306. Increasing the temperature of the drilling fluid 203 may impart energy to the gases entrained in the drilling fluid 203 to help separate such gases from the drilling fluid 203 and maintain the gases separated from the drilling fluid 203 while the drilling fluid 203 passes along the conduits 306, 308. The heater 328 may comprise a heat exchanger portion 330 operatively connected with the fluid conduit 306 and a heat source portion 332 operatively connected with the heat exchanger portion 330. The heat source portion 332 may be operable to generate and transfer heat to the heat exchanger portion 330, and the heat exchanger portion 330 may be operable to transfer the heat to the drilling fluid 203 flowing through the conduit 306. The heater 328 may be an electrical heater operable to generate heat via electrical coils forming at least a portion of the heat exchanger 330 to increase the temperature of the drilling fluid 203 passing through the conduit 306. The heater 328 may instead be a fluid heater, such as may be operable to communicate a high-temperature fluid through fluid passages forming at least a portion of the heat exchanger 330 to increase the temperature of the drilling fluid 203 passing through the conduit 306. The fluid conduit 306 may terminate with a suction strainer 230 or another filter disposed within the source 204 and submerged within the drilling fluid 203.

A flow rate sensor 334 may be connected along the fluid conduit 306 to monitor flow rate of the drilling fluid 203 being drawn from the source 204. The flow rate sensor 334 may be operable to measure volumetric and/or mass flow rate of the drilling fluid 203. Although the flow rate of the drilling fluid 203 drawn from the source 204 may be known or determined based on the flow rate of the motive gas through the venturi ejector 210, the flow rate sensor 334 may also or instead be utilized to determine the flow rate of the drilling fluid 203. For example, the flow rate sensor 334 may be utilized to compensate for changes in drilling fluid flow rates caused by changes in drilling fluid viscosity and/or the suction strainer 230 becoming clogged with solid particles. The flow rate sensor 334 may be an electrical flow rate sensor operable to generate an electrical signal or information indicative of the flow rate. The flow rate sensor 334 may be a Coriolis flowmeter, a turbine flowmeter, or an acoustic flowmeter, among other examples. The flow rate sensor 334 may be communicatively connected with the control workstation 192, such as may permit the control workstation 192 to receive the signals or information generated by the flow rate sensor 334 and process such signals according to the executable programs and/or instructions stored in the control workstation 192.

A remotely-operated fluid control valve 336 may be connected along the conduit 308 to selectively permit or prevent the drilling fluid 203 from being discharged into the gas-liquid separator 310. The fluid control valve 336 may be actuated remotely by a corresponding actuator operatively coupled with the fluid control valve 336. The fluid control valve 336 may be utilized to purge the venturi ejector 210, the conduit 306, and the strainer 230. For example, when in a closed-flow position, the fluid control valve 336 may prevent fluid flow through the fluid conduit 308 and cause the pressurized motive gas to be directed into the conduit 306 via the ejector inlet 220 and out of the conduit 306 via the strainer 230. The motive gas may purge, unclog, or otherwise clean the inlet 220, the conduit 306, and the strainer 230 from solid particles and/or other contaminants that may have clogged the inlet 220, the conduit 306, and the strainer 230. The pressurized motive gas may also purge other devices fluidly connected along the conduit 306, such as the valve 326, the heat exchanger 330, and the flow rate meter 334.

The fluid control valve 318 may be or comprise a fluid shut-off valve operable to control substantially clean and/or particle-free fluids. The fluid control valve 318 may be or comprise a ball valve, a needle valve, a globe valve, a butterfly valve, and/or another type of fluid control valve, which may be selectively opened or closed to permit or prevent fluid flow therethrough. The fluid control valves 326, 336 may be or comprise fluid shut-off valves operable to control contaminated fluids or fluids containing solid particles. The fluid control valves 326, 336 may be or comprise ball valves, sleeve valves, pinch valves, globe valves, butterfly valves, and/or other types of fluid control valves, which may be selectively opened or closed to permit or prevent fluid flow therethrough. The actuators of the valves 318, 326, 336 may be or comprise electric actuators, such as solenoids or motors, or fluid actuators, such as pneumatic or hydraulic cylinders or rotary actuators. The valve actuators may be communicatively connected with the control workstation 192, such as may permit the control workstation 192 to operate the valves 318, 326, 336 according to the executable programs and/or instructions stored in the control workstation 192.

The gas-liquid separator 310 may be operable to further release mud gases and/or separate the released mud gases and the motive gas from the liquid drilling fluid 203, which may include minute solid particles suspended therein. The gas-liquid separator 310 may be or comprise a fluid separation column or a vessel comprising a fluid inlet 342 fluidly connected with the conduit 308, a gas outlet 344 fluidly connected with the gas analyzer 206 via a conduit 338, a liquid (i.e., degassed fluid) outlet 346 fluidly connected with the source 204 or another drilling fluid destination, and a liquid (i.e., degassed fluid) outlet 348 fluidly connected with the fluid analyzer 260 via a conduit 372. The inlet 342 may comprise a pipe segment extending through a wall of the gas-liquid separator 310 terminating with a downward facing opening configured to discharge (e.g., disperse or splatter) the mixture of the liquid drilling fluid 203, the motive gas, and the released mud gases into the gas-liquid separator 310 in a generally downward direction, as indicated by arrows 340. The outlet 344 may comprise a pipe segment extending through the wall of the gas-liquid separator 310 comprising a plurality of openings configured to receive a mixture of the motive gas and the released mud gas and transfer the mixture into the fluid conduit 338. The outlet 346 may be or comprise an opening at the bottom of the gas-liquid separator 310.

The gas-liquid separator 310 may comprise a multi-stage demister 350 disposed between the inlet 342 and the outlet 344. The demister 350 may be operable to coalesce or aggregate the airborne particles or droplets of the drilling fluid passing through the gas-liquid separator 310 from the inlet 232 to the outlet 234, as indicated by arrows 242, until such airborne particles become heavy enough to fall downwards toward the outlet 346 of the gas-liquid separator 310, as indicated by arrows 244. The multi-stage demister 350 may comprise a series of demister pads or elements 352 (e.g., mesh screens, baffles) operable to coalesce the airborne drilling fluid particles and held in position by frame or support members 354. The drilling fluid particles coalesced by the demister 350 may fall toward the outlet 346 and into the source 204 or another drilling fluid destination, as indicated by the arrows 244. The coalesced drilling fluid 203 particles or droplets that fall downwardly toward the outlet 346, as indicated by the arrows 244, are substantially free of entrained gases and, thus, may be collectively referred to as "degassed drilling fluid."

The gas-liquid separator 310 may be partially disposed within the source 204 such that the outlet 346 is located beneath a surface 248 of the drilling fluid 203 located within the source 204. The hydrostatic pressure at the outlet 346 may form a fluid seal, such as may prevent or inhibit positive pressure within the gas-oil separator 310 from causing the airborne mixture of drilling fluid particles, the motive gas, and the released mud gases to flow out of the gas-liquid separator 310 via the outlet 346 and, thereby, cause the airborne mixture to flow upwardly through the demister 350 and into the gas outlet 344. The gases discharged via the gas outlet 344 may be conveyed along the conduit 338 to a piece of surface equipment (e.g., flare stack) or vented into the ambient atmosphere, as indicated by arrows 252.

As described above, the gases passing through the conduit 338 may be monitored and analyzed in real time by the gas analyzer 206 operatively connected along the conduit 338. The signals or information generated by the various sensors and analyzers of the gas analyzer 206 may be received and processed in real time by the control workstation 192 or another processing device, which, in turn, may control the mud systems or equipment of the wellsite system 100 based on the received signals or information.

The degassed drilling fluid falling toward the outlet 346 or otherwise being discharged from the gas-liquid separator 310 may be analyzed by the fluid analyzer 260, which may be fluidly connected with the gas-liquid separator 310. At least a portion of the degassed drilling fluid droplets falling through the gas-liquid separator 310 may be captured by a collection funnel 362 located beneath the demister 350 and directed or conveyed to a container 364 via a liquid outlet 348. The outlet 348 may comprise a pipe segment extending at a downward angle through the wall of the gas-liquid separator 310 between the collection funnel 362 and the container 364, such as may permit transfer of the degassed drilling fluid from the collection funnel 362 to the container 364. A fluid level sensor 366 may be mounted or otherwise disposed in association with the container 364 to measure level of degassed drilling fluid 368 collected within the container 364. Excess degassed drilling fluid 368 may be evacuated from the container 364 via an overflow drain 365. A pump 370 may be fluidly connected along a fluid conduit 372 extending between the container 364 and the fluid analyzer 260. The pump 370 may be selectively operable to transfer the degassed drilling fluid 368 from the container 364 into and/or through the fluid analyzer 260 to be analyzed. A pressure sensor 374 may be connected along the fluid conduit 372 to measure pressure of the degassed drilling fluid 368 passing through the fluid conduit 372. A remotely-operated fluid control valve 376 may be connected along the conduit 372 to selectively permit or prevent the degassed drilling fluid 368 from being introduced into the fluid analyzer 260. The fluid control valve 376 may be a needle valve, a metering valve, a globe valve, or another valve operable to selectively permit or prevent the degassed drilling fluid 368 from flowing into and/or through the fluid analyzer 260. The fluid control valve 376 may progressively or gradually open and close to control rate of fluid flow into and/or through the fluid analyzer 260. The degassed drilling fluid 368 passing through the fluid analyzer 260 may be discharged into the source 204 via a discharge fluid conduit 378.

At least a portion of the degassed drilling fluid 368 pumped through the fluid conduit 372 that is not passed through the fluid analyzer 260 may be diverted or discharged into the source 204 via a discharge fluid conduit 380. A remotely-operated fluid control valve 382 may be connected along the conduit relief fluid conduit 380 to selectively permit or prevent the degassed drilling fluid 368 from being diverted into the source 204. The pump 370 and valves 376, 382 may be selectively operated to purge or discharge old degassed drilling fluid 368 from the container 364, such as when the drilling fluid 368 has been sitting dormant in the container 364 at a high level for an extended or otherwise predetermined period of time, and to permit a new (i.e., fresh) batch of degassed drilling fluid 368 to be introduced into the container 364 for analysis by the fluid analyzer 260. During such purging operations the valve 382 may be open and the valve 376 may be closed.

The pump 370 and valves 376, 382 may be collectively operable to control flow rate of the degassed drilling fluid 368 flowing to and/or through the fluid analyzer 260. For example, the pump 370 may be a fixed displacement pump operable to pump the degassed drilling fluid 368 at a flow rate that is proportional to operating rate of the pump 370. Therefore, flow rate of the drilling fluid 368 may be controlled by adjusting operating rate of the prime mover (e.g., electrical motor) driving the pump 370. The pump 370 may also or instead be operated at a predetermined substantially constant rate, based on operating specifications of the fluid analyzer 260. Furthermore, a portion of the degassed drilling fluid 368 pumped by the pump 370 may also or instead be diverted into the source 204 by the valve 382 while an intended flow rate of the degassed drilling fluid 368 may be directed to the fluid analyzer 260 by the valve 376.

The fluid control valves 376, 382 may each be actuated remotely by a corresponding actuator operatively coupled with each fluid control valve 376, 382. The fluid level sensor 366, the pump 370, the pressure sensor 374, and the actuators of the fluid control valves 376, 382 may be communicatively connected with the control workstation 192 or another processing device, such as may permit the control workstation 192 to receive the signals or information generated by the sensors 366, 374, process the signals or information according to the executable programs and/or instructions stored in the control workstation 192, and transmit control signals to the pump 370 and/or the fluid control valves 376, 382 to control flow of the degassed drilling fluid 368 according to such programs and/or received signals or instructions.

As described above, the degassed drilling fluid 368 passing through the conduit 372 may be monitored and analyzed in real time by one or more portions of the fluid analyzer 260. The signals or information generated by the various sensors and analyzers of the fluid analyzer 260 may be received and processed in real time by the control workstation 192 or another processing device, which, in turn, may control the mud systems or equipment of the wellsite system 100 based on the received signals or information.

The gas-liquid separator 310 or the associated inlet 342 and/or outlets 344, 348 may be fluidly connected with the corresponding conduits 308, 338, 372 and/or the container 364 via flexible couplings 360 (e.g., flexible bellows couplings) or lengths of flexible conduit. The flexible couplings 360 may prevent or inhibit movement and/or mechanical vibrations from being transferred between the gas-liquid separator 310 and the conduits 308, 338, 372. The flexible couplings 360 may permit the gas-liquid separator 310 to be mounted or otherwise mechanically connected with one or more portions of the drilling fluid reconditioning equipment 169, while reducing or preventing mechanical vibrations from being transferred to the fluid conduits 308, 338, 372, the container 364, and other devices connected with the fluid conduits 308, 338, 372.

Figure 4:
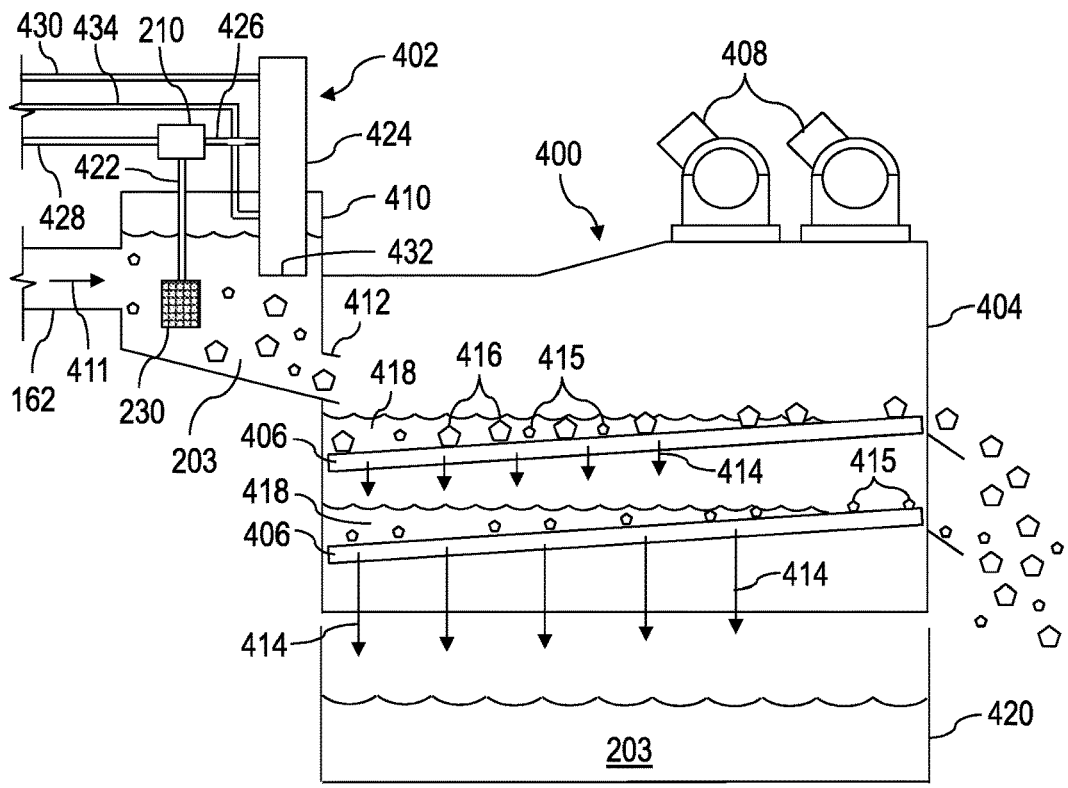
FIG. 4 is a schematic view of at least a portion of an example implementation of apparatus according to one or more aspects of the present disclosure.

FIG. 4 is a schematic view of a portion of a degasser 402 forming a portion of or mounted in association with a shale shaker 400 of the drilling fluid reconditioning equipment 169 according to one or more aspects of the present disclosure. The degasser 402 may comprise one or more features of the degassers 172, 202, 302 shown in FIGS. 1-3, respectively, including where indicated by like reference numbers, except as described below. The following description refers to FIGS. 1-4, collectively.

The shaker 400 may comprise a basket 404 containing a plurality of screen panels 406. One or more vibrating motors 408 may be fixedly connected to the basket 404. The shaker 400 may further comprise a header box 410 (i.e., a collection hopper) fluidly connected with the conduit 160 and operable to receive the drilling fluid 203 discharged from the wellbore 102, as indicated by arrow 411. The header box 410 may comprise a feeder 412 (i.e., an outlet), which may be configured for directing the drilling fluid 203 from the header box 410 into the basket 404 and distributing the drilling fluid 203 onto one or more of the screen panels 406. During shale shaker operations, the vibrating motors 408 may impart vibrations to the basket 404 and the screen panels 406 to cause the drilling fluid 203 and fine solid particles 415 to pass through an upper one of the screen panels 406, as indicated by arrows 414, and the larger solid particles 416 (e.g., drill cuttings) to move along the surface of the upper screen panel 406 until such solid particles 416 fall off the upper screen panel 406 into a solids container 143 (shown in FIG. 1). A lower one of the screen panels 406 may permit the drilling fluid 203 to pass, while transferring the finer solid particles 415 into the solids container 143. The drilling fluid 203 passing through the screen panels 406 may be collected within a drilling fluid container 420. The drilling fluid 203 within the basket 404 on top of the screen panels 406 may form a pond 418 (i.e., a drilling fluid pool) before passing through the screen panels 406.

The degasser 402 may be operable to release and/or separate formation and other gases entrained in drilling fluid 203 discharged from the wellbore 102. For example, at least a portion of the degasser 402 may be fluidly connected with the header box 410 (current drilling fluid source 204), such as may permit the degasser 402 to release and/or separate the gases entrained in the drilling fluid 203 contained within the header box 410. The degasser 402 may comprise a venturi ejector 210 fluidly connected with the header box 410 via a fluid conduit 422. The fluid conduit 422 may terminate with a suction strainer 230 located below the surface of the drilling fluid 203. The venturi ejector 210 may be fluidly connected with a motive gas source 212 (shown in FIGS. 2 and 3) via a fluid conduit 428. The degasser 402 may further comprise a gas-liquid separator 424 fluidly connected with the venturi ejector 210 via a fluid conduit 426. As described above, the venturi ejector 210 may be operable to move the drilling fluid 203 from the header box 410 to the gas-liquid separator 424 while receiving the motive gas from the motive gas source 212. The gas-liquid separator 424 may be operable to release and/or separate the gases entrained in the drilling fluid 203 received via the venturi ejector 210.

The gas-liquid separator 424 may comprise a drilling fluid inlet fluidly connected with the conduit 426, a gas outlet fluidly connected with a gas analyzer 206 (shown in FIGS. 2 and 3) via a conduit 430, a degassed drilling fluid outlet fluidly connected with a fluid analyzer 260 (shown in FIGS. 2 and 3) via a conduit 434, and a degassed drilling fluid outlet 432 fluidly connected with the header box 410. The liquid outlet 432 may comprise an opening at the bottom of the gas-liquid separator 424. The gas-liquid separator 424 may be mounted within the header box 410 such that the outlet 432 is located beneath the surface of the drilling fluid 203 located within the header box 410, such that the degassed drilling fluid 203 particles coalesced by the oil-gas separator 424 fall toward the liquid outlet 432 and into the header box 410. As described above, the hydrostatic pressure at the outlet 432 may form a fluid seal, which may prevent or inhibit the positive pressure within the gas-oil separator 424 from causing the airborne mixture of drilling fluid particles, the motive gas, and the released gases to flow out of the gas-liquid separator 424 via the liquid outlet 432 and may cause the airborne mixture to flow upwardly through the gas-liquid separator 424 and out of the gas-liquid separator 424 via the conduit 430. As further described above, the gases passing through the conduit 430 may be analyzed by the gas analyzer 206 fluidly connected along the conduit 430, and at least a portion of the degassed drilling fluid from the gas-liquid separator 424 may be directed to the fluid analyzer 260 for analysis via the conduit 434.

Although not shown in FIG. 4 for clarity and ease of understanding, the degasser 402 may comprise additional components of the degassers 202, 302 shown in FIGS. 2 and 3. For example, the degasser 402 may comprise various sensors, fluid treatment devices, and fluid control devices shown in FIGS. 2 and 3 fluidly connected along corresponding conduits 422, 426, 428, 430, 434.

Figure 5:
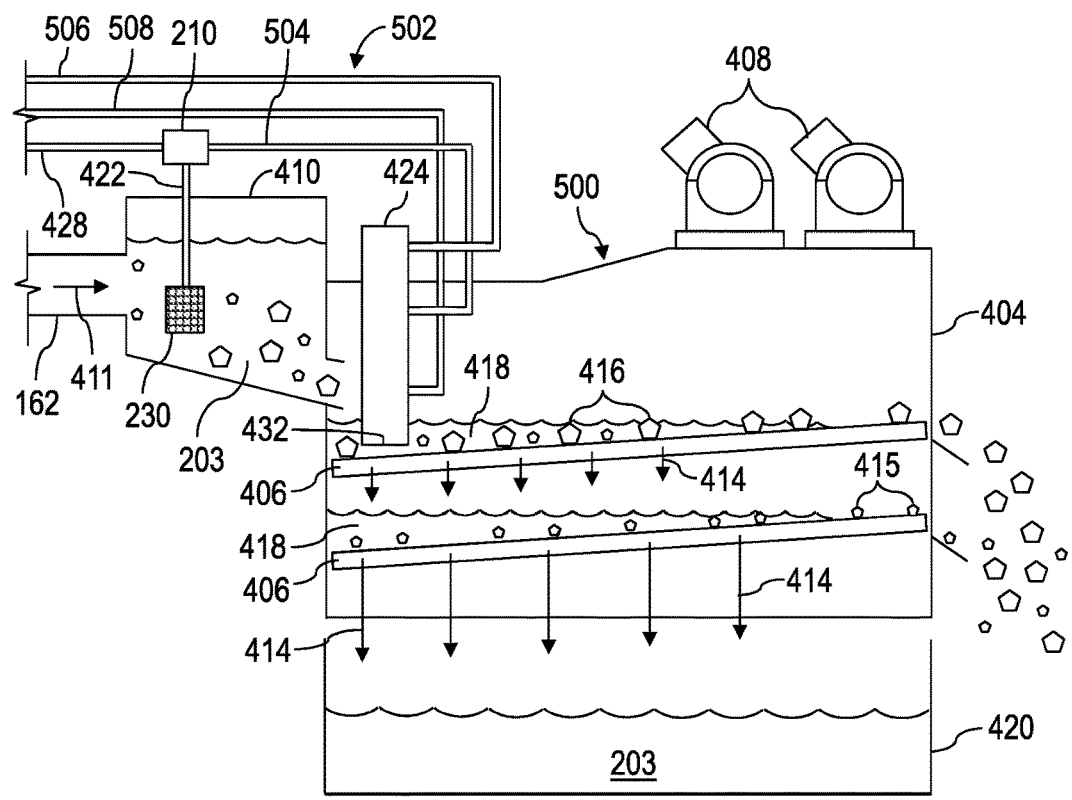
FIG. 5 is a schematic view of at least a portion of an example implementation of apparatus according to one or more aspects of the present disclosure.

FIG. 5 is a schematic view of a portion of a degasser 502 forming a portion of or mounted in association with a shale shaker 500 of the drilling fluid reconditioning equipment 169 according to one or more aspects of the present disclosure. The degasser 502 may comprise one or more features of the degassers 172, 202, 302, 402 shown in FIGS. 1-4, respectively, including where indicated by like reference numbers, except as described below. The following description refers to FIGS. 1-5, collectively.

Unlike the degasser 402 shown in FIG. 4, the degasser 502 may comprise a gas-liquid separator 424 fluidly connected with a drilling fluid pond 418 (e.g., collection area) formed within a basket 404 of the shale shaker 500. For example, the gas-liquid separator 424 may be mounted within the basket 404 such that outlet 432 is located beneath the surface of the drilling fluid pond 418 located within the basket 404 on the surface of a screen panel 406. Accordingly, the drilling fluid 203 received and coalesced by the oil-gas separator 424 may fall toward the outlet 432 of the gas-liquid separator 424 and into the pond 418.

The gas-liquid separator 424 may be mounted to the basket 404, which may facilitate transfer of vibrations from the shale shaker 500 to the gas-liquid separator 424. The vibrations may facilitate automatic cleaning of internal components of the gas-liquid separator 424 and/or assist separation and/or release of the gases from the drilling fluid 203. For example, the vibrations may loosen solid particles which may contaminate or clog up the demister 240, 350 (shown in FIGS. 2 and 3). The gas-liquid separator 424 may be fluidly connected with the venturi ejector 210 via a fluid conduit 504, with the gas analyzer 206 (shown in FIGS. 2 and 3) via a fluid conduit 506, and with the fluid analyzer 260 (shown in FIGS. 2 and 3) via a fluid conduit 508. The fluid conduits 504, 506, 508 may be flexible conduits or the gas-liquid separator 424 may be connected with the fluid conduits 504, 506, 508 via flexible couplings 360 (shown in FIG. 3), such as may prevent or inhibit the mechanical vibrations from being transferred to the venturi ejector 210 and other devices connected with the conduits 504, 506, 508. Although the shale shakers 400, 500 are shown as multi-deck shale shakers, it is to be understood that the degassers 402, 502 may be installed in association with a single-deck shale shakers or other shale shakers that may be utilized with or form a portion of the drilling fluid reconditioning equipment 169.

Figure 6:
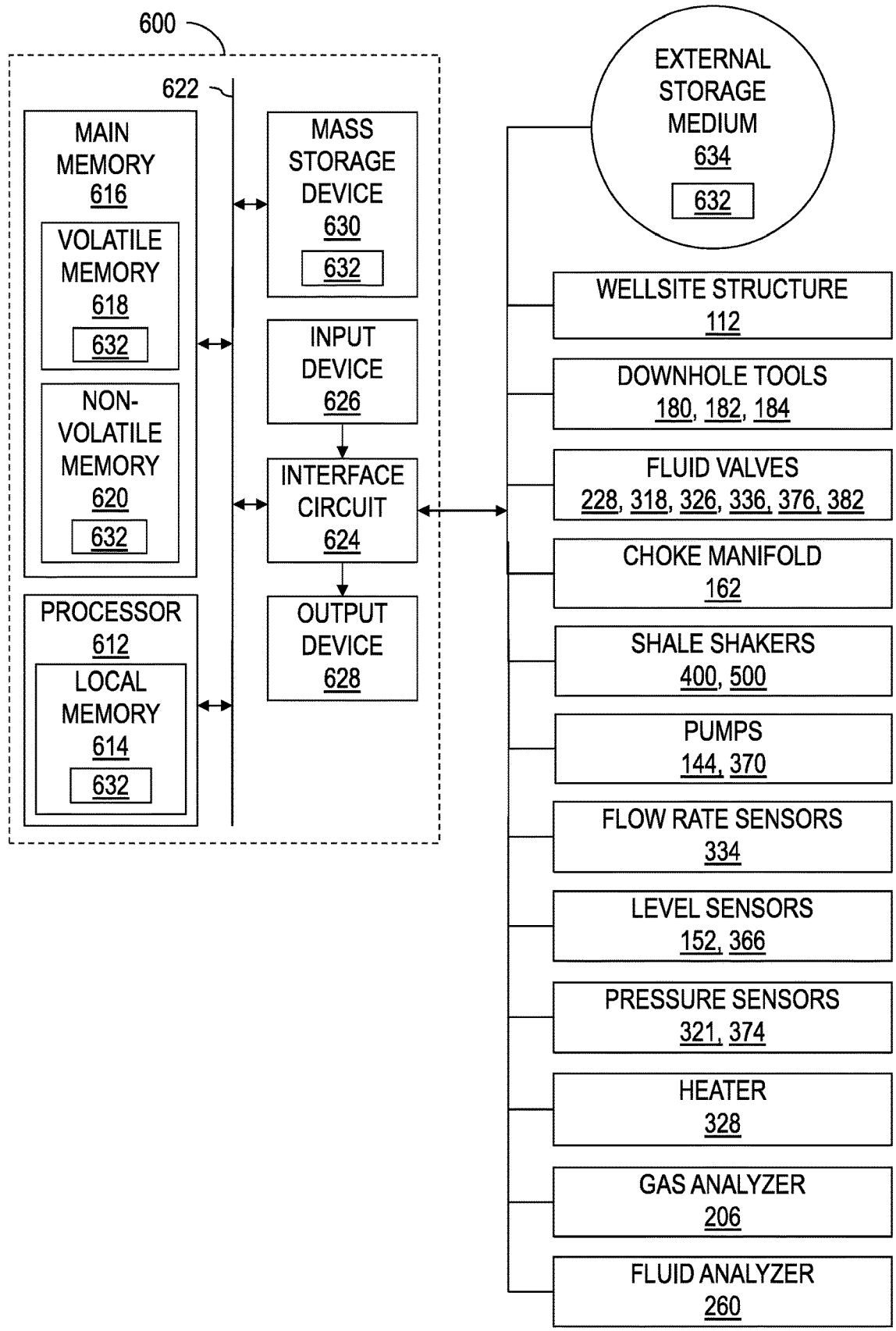
FIG. 6 is a schematic view of at least a portion of an example implementation of apparatus according to one or more aspects of the present disclosure.

FIG. 6 is a schematic view of at least a portion of an example implementation of a processing device 600 according to one or more aspects of the present disclosure. The processing device 600 may be in communication with the wellsite structure 112, the downhole tools 180, 182, 184, the fluid control valves 228, 318, 326, 336, 376, 382, the choke manifold 162, the shale shaker 400, 500, the pumps 144, 370, the flow rate sensors 334, the fluid level sensors 152, 366, the pressure sensors 321, 374, the heater 328, the gas analyzer 206, the fluid analyzer 260, and/or actuators associated with one or more of these components. For clarity, these and other components in communication with the processing device 600 will be collectively referred to hereinafter as "sensor and controlled equipment." Accordingly, the following description refers to FIGS. 1-6, collectively.

The processing device 600 may be operable to receive coded instructions 632 from the wellsite operators 194 and signals generated by the sensor equipment, process the coded instructions 632 and the signals, and communicate control signals to the controlled equipment to execute the coded instructions 632 to implement at least a portion of one or more example methods and/or operations described herein, and/or to implement at least a portion of one or more of the example systems described herein. The processing device 600 may be or form a portion of the control workstation 192.

The processing device 600 may be or comprise, for example, one or more processors, special-purpose computing devices, servers, personal computers (e.g., desktop, laptop, and/or tablet computers) personal digital assistant (PDA) devices, smartphones, internet appliances, and/or other types of computing devices. The processing device 600 may comprise a processor 612, such as a general-purpose programmable processor. The processor 612 may comprise a local memory 614, and may execute coded instructions 632 present in the local memory 614 and/or another memory device. The processor 612 may execute, among other things, the machine-readable coded instructions 632 and/or other instructions and/or programs to implement the example methods and/or operations described herein. The programs stored in the local memory 614 may include program instructions or computer program code that, when executed by an associated processor, facilitate the wellsite system 100 and/or the drilling fluid analysis systems 170, 200, 300 to perform the example methods and/or operations described herein. The processor 612 may be, comprise, or be implemented by one or more processors of various types suitable to the local application environment, and may include one or more of general-purpose computers, special-purpose computers, microprocessors, digital signal processors (DSPs), field-programmable gate arrays (FPGAs), application-specific integrated circuits (ASICs), and processors based on a multi-core processor architecture, as non-limiting examples. Of course, other processors from other families are also appropriate.

The processor 612 may be in communication with a main memory 616, such as may include a volatile memory 618 and a non-volatile memory 620, perhaps via a bus 622 and/or other communication means. The volatile memory 618 may be, comprise, or be implemented by random access memory (RAM), static random access memory (SRAM), synchronous dynamic random access memory (SDRAM), dynamic random access memory (DRAM), RAMBUS dynamic random access memory (RDRAM), and/or other types of random access memory devices. The non-volatile memory 620 may be, comprise, or be implemented by read-only memory, flash memory, and/or other types of memory devices. One or more memory controllers (not shown) may control access to the volatile memory 618 and/or non-volatile memory 620.

The processing device 600 may also comprise an interface circuit 624. The interface circuit 624 may be, comprise, or be implemented by various types of standard interfaces, such as an Ethernet interface, a universal serial bus (USB), a third generation input/output (3GIO) interface, a wireless interface, a cellular interface, and/or a satellite interface, among others. The interface circuit 624 may also comprise a graphics driver card. The interface circuit 624 may also comprise a communication device, such as a modem or network interface card to facilitate exchange of data with external computing devices via a network (e.g., Ethernet connection, digital subscriber line (DSL), telephone line, coaxial cable, cellular telephone system, satellite, etc.). One or more of the controlled equipment may be connected with the processing device 600 via the interface circuit 624, such as may facilitate communication between the controlled equipment and the processing device 600.

One or more input devices 626 may also be connected to the interface circuit 624. The input devices 626 may permit the wellsite operators 194 to enter the coded instructions 632, such as control commands, processing routines, and input data. The input devices 626 may be, comprise, or be implemented by a keyboard, a mouse, a touchscreen, a track-pad, a trackball, an isopoint, and/or a voice recognition system, among other examples. One or more output devices 628 may also be connected to the interface circuit 624. The output devices 628 may be, comprise, or be implemented by display devices (e.g., a liquid crystal display (LCD), a light-emitting diode (LED) display, or cathode ray tube (CRT) display), printers, and/or speakers, among other examples. The processing device 600 may also communicate with one or more mass storage devices 630 and/or a removable storage medium 634, such as may be or include floppy disk drives, hard drive disks, compact disk (CD) drives, digital versatile disk (DVD) drives, and/or USB and/or other flash drives, among other examples.

The coded instructions 632 may be stored in the mass storage device 630, the main memory 616, the local memory 614, and/or the removable storage medium 634. Thus, the processing device 600 may be implemented in accordance with hardware (perhaps implemented in one or more chips including an integrated circuit, such as an ASIC), or may be implemented as software or firmware for execution by the processor 612. In the case of firmware or software, the implementation may be provided as a computer program product including a non-transitory, computer-readable medium or storage structure embodying computer program code (i.e., software or firmware) thereon for execution by the processor 612. The coded instructions 632 may include program instructions or computer program code that, when executed by the processor 612, may cause the wellsite system 100 and/or the drilling fluid analysis systems 170, 200, 300 to perform intended methods, processes, and/or operations disclosed herein.

Figure 7:
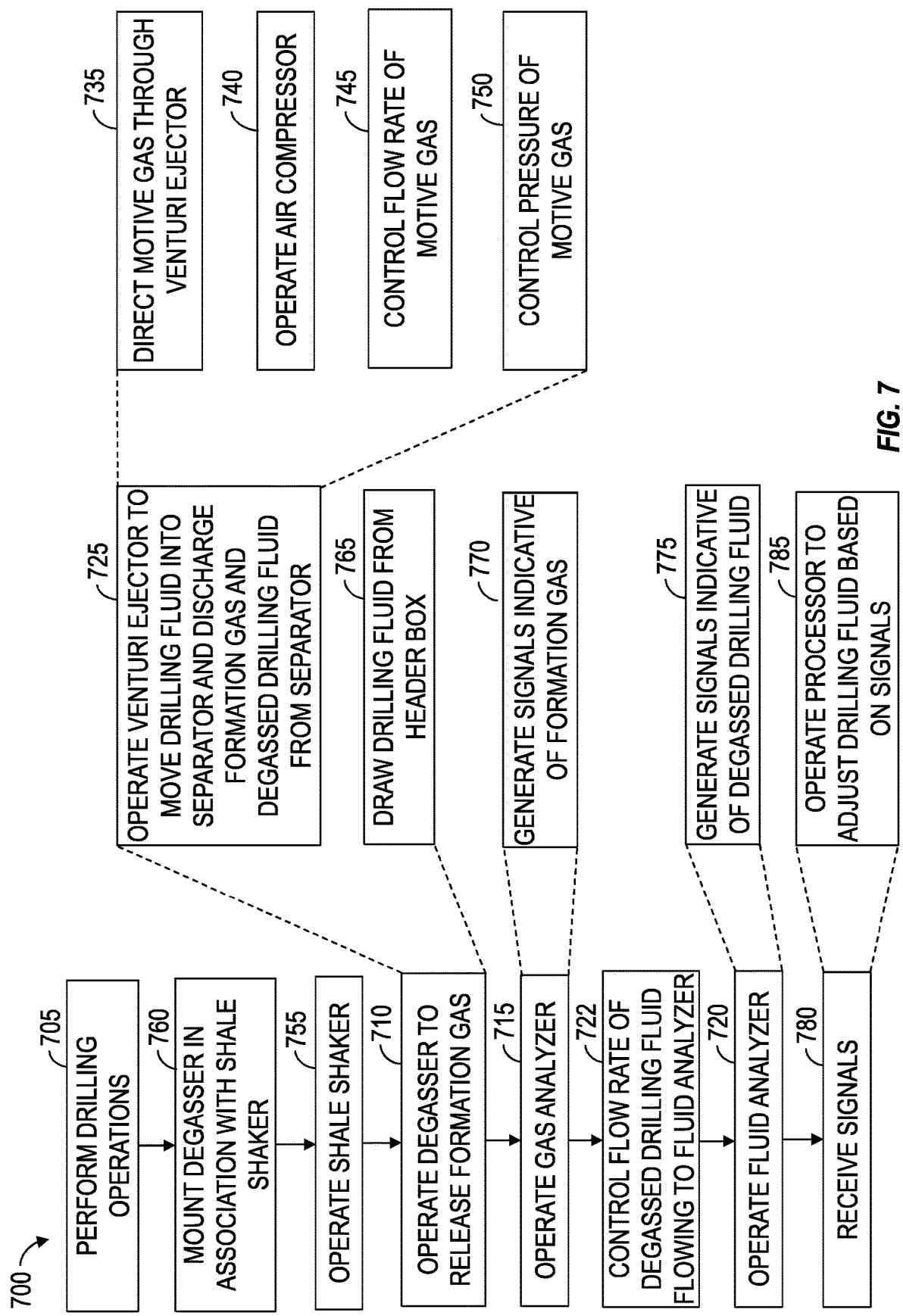
FIG. 7 is a flow-chart diagram of at least a portion of an example implementation of a method according to one or more aspects of the present disclosure.

FIG. 7 is a flow-chart diagram of at least a portion of an example implementation of a method (700) according to one or more aspects of the present disclosure. The method (700) described below and/or other operations described herein may be performed utilizing or otherwise in conjunction with at least a portion of one or more implementations of one or more instances of the apparatus shown in one or more of FIGS. 1-6 and/or otherwise within the scope of the present disclosure. However, the method (700) and operations described herein may be performed in conjunction with implementations of apparatus other than those depicted in FIGS. 1-6 that are also within the scope of the present disclosure. The method (700) and operations may be performed manually by one or more wellsite operators 194 and/or performed or caused, at least partially, by the processing device 600 executing the coded instructions 632 according to one or more aspects of the present disclosure. For example, the processing device 600 may receive input signals and automatically generate and transmit output signal to operate or cause a change in an operational parameter of one or more pieces of the wellsite equipment described above. However, the wellsite operator 194 may also or instead manually operate the one or more pieces of wellsite equipment via the processing device 600 based on sensor signals displayed.

The method (700) may comprise performing (705) drilling operations to form a wellbore 102 at an oil and gas wellsite 104, operating (710) a degasser 172, 202, 302 at the oil and gas wellsite 104 to release and separate mud gas entrained in drilling fluid 203 discharged from the wellbore 102, operating (715) a gas analyzer 206 to mud gas discharged from the degasser 172, 202, 302, and operating (720) a fluid analyzer 260 to analyze degassed drilling fluid discharged from the degasser 172, 202, 302. The method (700) may further comprise controlling (722) flow rate of the degassed drilling fluid flowing to the fluid analyzer 260, such as via a pump 370 and/or fluid control valves 376, 382.

Operating (710) the degasser 202, 302 to release and separate the mud gas entrained in the drilling fluid 203 discharged from the wellbore 102 may comprise operating (725) a venturi ejector 210 to move the drilling fluid 203 containing the entrained mud gas from a drilling fluid source 160, 204, 410 into a gas-liquid separator 214, 310 causing the mud gas and the degassed drilling fluid 368 to be discharged from the gas-liquid separator 214, 310. The venturi ejector 210 may be or comprises an eductor. The gas analyzer 206 may comprise a gas chromatography analyzer 256, whereby operating (715) the gas analyzer 206 may comprise performing quantitative gas analysis. 70.

Operating (725) the venturi ejector 210 may comprise directing (735) motive gas through the venturi ejector 210 to form a vacuum to draw the drilling fluid 203 from the drilling fluid source 160, 204, 410 and to discharge the drilling fluid 203 into the gas-liquid separator 214, 310. Drawing the drilling fluid 203 from the drilling fluid source 160, 204, 410 may be performed via a suction strainer 230 disposed within the drilling fluid source 160, 204, 410.

Operating (725) the venturi ejector 210 may further comprise operating (740) a gas compressor 212. Operating (725) the venturi ejector 210 may cause diffusion of the drilling fluid 203 into airborne droplets to release the entrained mud gas from the drilling fluid 203 while the drilling fluid 203 moves through the venturi ejector 210. Operating (725) the venturi ejector 210 may also comprise: operating (745) a flow rate control valve 228, 322 to control rate of the motive gas flowing through the venturi ejector 210 to control rate of the drilling fluid 203 drawn from the drilling fluid source 160, 204, 410; and/or operating (750) a pressure control valve 228 to control pressure of the motive gas flowing into the venturi ejector 210 to control rate of the drilling fluid 203 drawn from the drilling fluid source 160, 204, 410.

The method (700) may further comprise operating (755) a shale shaker 400, 500 to remove solid particles 141 from the drilling fluid 203 discharged from the wellbore 102. Prior to operating (755) the shale shaker 400, 500, the method (700) may further comprise mounting (760) the degasser 172, 202, 302 in association with the shale shaker 400, 500, whereby operating the degasser 172, 202, 302 may comprise drawing (765) the drilling fluid 203 from a header box 410 of the shale shaker 400, 500.

Operating (715) the gas analyzer 206 may comprises generating (770) first signals or information indicative of type and/or quantity of the mud gas and operating (720) the fluid analyzer 260 may comprise generating (775) second signals or information indicative of properties and/or characteristics of the degassed drilling fluid 368. Thus, the method (700) may further comprise receiving (780) the first and second signals or information by a processing device 600, and operating (785) the processing device 600 to cause wellsite equipment 110, 169 at the oil and gas wellsite 104 to adjust properties of drilling fluid being injected into the wellbore 102 via a drill string 120 during the drilling operations (705) based at least in part on the received first and second signals or information.

In view of the entirety of the present disclosure, including the figures and the claims, a person having ordinary skill in the art will readily recognize that the present disclosure introduces an apparatus comprising a degasser operable to release and separate mud gas entrained in drilling fluid discharged from a wellbore at an oil and gas wellsite, wherein the degasser comprises: a gas-liquid separator comprising a separator inlet configured to receive the drilling fluid containing the entrained mud gas, a first separator outlet configured to discharge the mud gas, and a second separator outlet configured to discharge degassed drilling fluid; and a venturi ejector operable to move the drilling fluid containing the entrained mud gas from a drilling fluid source to the gas-liquid separator, wherein the venturi ejector comprises a first ejector inlet configured to fluidly connect with a motive gas source, a second ejector inlet configured to fluidly connect with the drilling fluid source, and an ejector outlet fluidly connected with the separator inlet.

The gas-liquid separator may comprise a vessel containing a demister located between the separator inlet and the first separator outlet.

The second separator outlet may be configured to be fluidly connected with a drilling fluid destination, and the gas-liquid separator may be configured to be positioned at least partially within the drilling fluid destination such that the second separator outlet is located below surface of the drilling fluid within the drilling fluid destination.

The degasser may comprise a strainer fluidly connected with the second ejector inlet and configured to be disposed within the drilling fluid source.

The degasser may be configured to be mounted in association with a shale shaker. The shale shaker may comprise a header box, and the drilling fluid source may be or comprise the header box. The second separator outlet may be configured to discharge the degassed drilling fluid into the header box. The shale shaker may comprise a basket, and the second separator outlet may be configured to discharge the degassed drilling fluid into the basket.

The motive gas source may be or comprise a gas compressor.

The venturi ejector may be or comprise an eductor.

The venturi ejector may be operable to: receive pressurized motive gas via the first ejector inlet; form a vacuum at the second ejector inlet to draw the drilling fluid via the second ejector inlet; and discharge a mixture of the motive gas and the drilling fluid via the ejector outlet.

The venturi ejector may be operable to diffuse the drilling fluid into airborne droplets to release the entrained mud gas while the drilling fluid is discharged from the venturi ejector.

The degasser may comprise a flow rate control valve fluidly connected along a fluid conduit extending between the first ejector inlet of the venturi ejector and the motive gas source, and the flow rate control valve may be operable to control rate of the motive gas flowing through the venturi ejector to control rate of the drilling fluid being moved from the drilling fluid source to the gas-liquid separator.

The degasser may further comprise: a pressure control valve fluidly connected along a fluid conduit extending between the first ejector inlet of the venturi ejector and the motive gas source; and a fixed orifice valve fluidly connected along the fluid conduit between the first ejector inlet of the venturi ejector and the pressure control valve, wherein the pressure control valve and the fixed orifice valve may be collectively operable to control rate of the motive gas flowing through the venturi ejector to control rate of the drilling fluid being moved from the drilling fluid source to the gas-liquid separator.

The degasser may comprise a heater operatively connected between the drilling fluid source and the gas-liquid separator, and the heater may be operable to heat the drilling fluid flowing between the drilling fluid source and the gas-liquid separator.

The degasser may comprise a valve fluidly connected along a fluid conduit extending between the ejector outlet of the venturi ejector and the separator inlet of the gas-liquid separator, the valve may be operable to selectively permit or prevent fluid flow through the fluid conduit, and in a closed position the valve may cause motive gas entering the venturi ejector to be discharged via the second ejector inlet to purge the venturi ejector and a fluid conduit extending between the second ejector inlet and the drilling fluid source.

The apparatus may further comprise a gas analyzer fluidly connected with the first separator outlet, and the gas analyzer may be operable to generate signals or information indicative of type and/or quantity of the mud gas released and separated from the drilling fluid. The gas analyzer may be or comprise a gas chromatography analyzer. The apparatus may further comprise a fluid analyzer fluidly connected with the second separator outlet, wherein the fluid analyzer may be operable to generate signals or information indicative of properties and/or characteristics of the degassed drilling fluid. The apparatus may further comprise a controller comprising a processor and a memory storing an executable computer program code, wherein the controller may be communicatively connected with the gas analyzer and fluid analyzer and operable to: receive the signals or information generated by the gas analyzer and fluid analyzer; and cause wellsite equipment at the oil and gas wellsite to adjust properties of drilling fluid that is to be injected into the wellbore via a drill string during drilling operations based at least partially on the received signals or information. The gas-liquid separator may further comprise a third separator outlet configured to discharge the degassed drilling fluid into a drilling fluid destination.

The present disclosure also introduces an apparatus comprising a drilling fluid analysis system comprising: (A) a gas analyzer; (B) a fluid analyzer; and (C) a degasser operable to release and separate mud gas entrained in drilling fluid discharged from a wellbore at an oil and gas wellsite, wherein the degasser comprises a gas-liquid separator comprising: (i) a separator inlet configured to receive the drilling fluid containing the entrained mud gas; (ii) a first separator outlet for discharging the mud gas fluidly connected with the gas analyzer; and (iii) a second separator outlet for discharging degassed drilling fluid fluidly connected with the fluid analyzer.

The gas-liquid separator may comprise a vessel containing a demister located between the separator inlet and the first separator outlet.

The second separator outlet may be configured to be fluidly connected with a drilling fluid destination, and the gas-liquid separator may be configured to be positioned at least partially within the drilling fluid destination such that the second separator outlet is located below surface of the drilling fluid within the drilling fluid destination.

The degasser may comprise a strainer fluidly connected with the second ejector inlet and configured to be disposed within the drilling fluid source.

The degasser may be configured to be mounted in association with a shale shaker. The shale shaker may comprise a header box, and the drilling fluid source may be or comprise the header box. The second separator outlet may be configured to discharge the degassed drilling fluid into the header box. The shale shaker may comprise a basket, and the second separator outlet may be configured to discharge the degassed drilling fluid into the basket.

The motive gas source may be or comprise a gas compressor.

The degasser may comprise a venturi ejector operable to move the drilling fluid containing the entrained mud gas from a drilling fluid source to the gas-liquid separator. The venturi ejector may comprise: a first ejector inlet configured to fluidly connect with a motive gas source; a second ejector inlet configured to fluidly connect with the drilling fluid source; and an ejector outlet fluidly connected with the separator inlet. The venturi ejector may be or comprise an eductor. The venturi ejector may be operable to: receive pressurized motive gas via the first ejector inlet; form a vacuum at the second ejector inlet to draw the drilling fluid via the second ejector inlet; and discharge a mixture of the motive gas and the drilling fluid via the ejector outlet. The venturi ejector may be operable to diffuse the drilling fluid into airborne droplets to release the entrained mud gas while the drilling fluid is discharged from the venturi ejector. The degasser may comprise a flow rate control valve fluidly connected along a fluid conduit extending between the first ejector inlet of the venturi ejector and the motive gas source, and the flow rate control valve may be operable to control rate of the motive gas flowing through the venturi ejector to control rate of the drilling fluid being moved from the drilling fluid source to the gas-liquid separator. The degasser may comprise: a pressure control valve fluidly connected along a fluid conduit extending between the first ejector inlet of the venturi ejector and the motive gas source; and a fixed orifice valve fluidly connected along the fluid conduit between the first ejector inlet of the venturi ejector and the pressure control valve, wherein the pressure control valve and the fixed orifice valve may be collectively operable to control rate of the motive gas flowing through the venturi ejector to control rate of the drilling fluid being moved from the drilling fluid source to the gas-liquid separator. The degasser may comprise a heater operatively connected between the drilling fluid source and the gas-liquid separator, and the heater may be operable to heat the drilling fluid flowing between the drilling fluid source and the gas-liquid separator. The degasser may comprise a valve fluidly connected along a fluid conduit extending between the ejector outlet of the venturi ejector and the separator inlet of the gas-liquid separator, wherein the valve may be operable to selectively permit or prevent fluid flow through the fluid conduit, and in a closed position the valve may cause motive gas entering the venturi ejector to be discharged via the second ejector inlet to purge the venturi ejector and a fluid conduit extending between the second ejector inlet and the drilling fluid source.

The gas analyzer may be operable to generate first signals or information indicative of type and/or quantity of the mud gas released and separated from the drilling fluid, and the fluid analyzer may be operable to generate second signals or information indicative of properties and/or characteristics of the degassed drilling fluid. The gas analyzer may be or comprise a gas chromatography analyzer. The apparatus may further comprise a controller comprising a processor and a memory storing an executable computer program code, and the controller may be communicatively connected with the gas analyzer and fluid analyzer and operable to: receive the first and second signals or information; and cause wellsite equipment at the oil and gas wellsite to adjust properties of drilling fluid that is to be injected into the wellbore via a drill string during drilling operations based at least partially on the received first and second signals or information. The gas-liquid separator may comprise a third separator outlet configured to discharge the degassed drilling fluid into a drilling fluid destination.

The present disclosure also introduces an apparatus comprising a shale shaker operable to remove solid particles from drilling fluid discharged from a wellbore at an oil and gas wellsite, wherein the shale shaker comprises: a header box operable to receive the drilling fluid; a basket; a screen disposed within the basket; and a degasser operable to release and separate mud gas entrained in the drilling fluid received into the header box, wherein the degasser comprises: (i) a gas-liquid separator comprising a separator inlet configured to receive the drilling fluid containing the entrained mud gas, a first separator outlet configured to discharge the mud gas, and a second separator outlet configured to discharge degassed drilling fluid; and (ii) a venturi ejector operable to move the drilling fluid from the header box to the gas-liquid separator, wherein the venturi ejector may comprise a first ejector inlet configured to fluidly connect with a motive gas source, a second ejector inlet fluidly connected with the header box, and an ejector outlet fluidly connected with the separator inlet.

The gas-liquid separator may comprise a vessel containing a demister located between the separator inlet and the first separator outlet.

The gas-liquid separator may be operable to be positioned at least partially within the drilling fluid destination such that the second separator outlet is located below surface of the drilling fluid within the drilling fluid destination.

The drilling fluid destination may be or comprise the header box.

The drilling fluid destination may be or comprise a portion of the basket operable to form a drilling fluid pond.

The motive gas source may be or comprise a gas compressor.

The venturi ejector may be or comprise an eductor.

The venturi ejector may be operable to: receive pressurized motive gas via the first ejector inlet; form a vacuum at the second ejector inlet to draw the drilling fluid via the second ejector inlet; and discharge a mixture of the motive gas and the drilling fluid via the ejector outlet.

The venturi ejector may be operable to diffuse the drilling fluid into airborne droplets to release the entrained mud gas while the drilling fluid is discharged from the venturi ejector.

The degasser may comprise a flow rate control valve fluidly connected along a fluid conduit extending between the first ejector inlet of the venturi ejector and the motive gas source, and the flow rate control valve may be operable to control rate of the motive gas flowing through the venturi ejector to control rate of the drilling fluid being moved from the drilling fluid source to the gas-liquid separator.

The degasser may comprise: a pressure control valve fluidly connected along a fluid conduit extending between the first ejector inlet of the venturi ejector and the motive gas source; and a fixed orifice valve fluidly connected along the fluid conduit between the first ejector inlet of the venturi ejector and the pressure control valve, wherein the pressure control valve and the fixed orifice valve may be collectively operable to control rate of the motive gas flowing through the venturi ejector to control rate of the drilling fluid being moved from the drilling fluid source to the gas-liquid separator.

The degasser may comprise a heater operatively connected along a fluid conduit extending between the second ejector inlet of the venturi ejector and the drilling fluid source, and the heater may be operable to heat the drilling fluid flowing through the fluid conduit.

The degasser may comprise a valve fluidly connected along a fluid conduit extending between the ejector outlet of the venturi ejector and the separator inlet of the gas-liquid separator, the valve may be operable to selectively permit or prevent fluid flow through the fluid conduit, and in a closed position the valve may cause motive gas entering the venturi ejector to be discharged via the second ejector inlet to purge the venturi ejector and a fluid conduit extending between the second ejector inlet and the drilling fluid source.

The apparatus may further comprise a gas analyzer fluidly connected with the first separator outlet, and the gas analyzer may be operable to generate signals or information indicative of type and/or quantity of the mud gas released and separated from the drilling fluid. The gas analyzer may be or comprise a gas chromatography analyzer. The apparatus may further comprise a fluid analyzer fluidly connected with the second separator outlet, and the fluid analyzer may be operable to generate signals or information indicative of properties and/or characteristics of the degassed drilling fluid. The apparatus may further comprise a controller comprising a processor and a memory storing an executable computer program code, and the controller may be communicatively connected with the gas analyzer and fluid analyzer and operable to: receive the signals or information from the gas analyzer and fluid analyzer; and cause wellsite equipment at the oil and gas wellsite to adjust properties of drilling fluid that is to be injected into the wellbore via a drill string during drilling operations based at least partially on the received signals or information. The gas-liquid separator may comprise a third separator outlet configured to discharge the degassed drilling fluid into a drilling fluid destination.

The present disclosure also introduces a method comprising: performing drilling operations to form a wellbore at an oil and gas wellsite; operating a degasser at the oil and gas wellsite to release and separate mud gas entrained in drilling fluid discharged from the wellbore; operating a gas analyzer to analyze the mud gas discharged from the degasser; and operating a fluid analyzer to analyze degassed drilling fluid discharged from the degasser.

Operating the degasser to release and separate the mud gas entrained in the drilling fluid discharged from the wellbore may comprise operating a venturi ejector to move the drilling fluid containing the entrained mud gas from a drilling fluid source into a gas-liquid separator causing the mud gas and the degassed drilling fluid to be discharged from the gas-liquid separator. The venturi ejector may be or comprise an eductor. Operating the venturi ejector may comprise directing motive gas through the venturi ejector to: form a vacuum to draw the drilling fluid from the drilling fluid source; and discharge the drilling fluid into the gas-liquid separator. Operating the venturi ejector may comprise operating a gas compressor. Operating the venturi ejector may cause diffusion of the drilling fluid into airborne droplets to release the entrained mud gas from the drilling fluid while the drilling fluid moves through the venturi ejector. Operating the venturi ejector may comprise operating a flow rate control valve to control rate of the motive gas flowing through the venturi ejector to control rate of the drilling fluid drawn from the drilling fluid source. Operating the venturi ejector may comprise operating a pressure control valve to control pressure of the motive gas flowing into the venturi ejector to control rate of the drilling fluid drawn from the drilling fluid source. Drawing the drilling fluid from the drilling fluid source may be performed via a suction strainer disposed within the drilling fluid source.

The method may further comprise controlling flow rate of the degassed drilling fluid flowing to the fluid analyzer.

The method may further comprise operating a shale shaker to remove solid particles from the drilling fluid discharged from the wellbore. Operating the degasser may comprise drawing the drilling fluid from a header box of the shale shaker. The method may further comprise, prior to operating the shale shaker, mounting the degasser in association with the shale shaker.

Operating the gas analyzer may comprise generating first signals or information indicative of type and/or quantity of the mud gas, operating the fluid analyzer may comprise generating second signals or information indicative of properties and/or characteristics of the degassed drilling fluid, and the method may further comprise: receiving the first and second signals or information by a processing device; and operating the processing device to cause wellsite equipment at the oil and gas wellsite to adjust properties of drilling fluid being injected into the wellbore via a drill string during the drilling operations based at least in part on the received first and second signals or information.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same purposes and/or achieving the same advantages of the embodiments introduced herein. A person having ordinary skill in the art should also realize that such equivalent constructions do not depart from the scope of the present disclosure, and that they may make various changes, substitutions and alterations herein without departing from the spirit and scope of the present disclosure.

The Abstract at the end of this disclosure is provided to permit the reader to quickly ascertain the nature of the technical disclosure. It is submitted with the understanding that it will not be used to interpret or limit the scope or meaning of the claims.

What is claimed is:

1. An apparatus comprising:
   a degasser operable to release and separate mud gas entrained in drilling fluid discharged from a wellbore at an oil and gas wellsite, wherein the degasser comprises:
      a gas-liquid separator comprising a fluid separator housing comprising a separator inlet configured to receive the drilling fluid containing the entrained mud gas, a first separator outlet configured to discharge the mud gas, and a second separator outlet configured to discharge degassed drilling fluid, wherein the second separator outlet is configured to be fluidly connected with a drilling fluid destination, wherein the drilling fluid destination comprises a container configured to contain the drilling fluid, and wherein a bottom end of the fluid separator housing is positioned at least partially within the container of the drilling fluid destination such that the second separator outlet is located below a level of the container to which the drilling fluid is filled when contained within the container of the drilling fluid destination; and
      a venturi ejector operable to move the drilling fluid containing the entrained mud gas from the container of the drilling fluid destination to the gas-liquid separator, wherein the venturi ejector comprises a first ejector inlet configured to fluidly connect with a motive gas source, a second ejector inlet configured to fluidly connect with the container of the drilling fluid destination, and an ejector outlet fluidly connected with the separator inlet.

2. The apparatus of claim 1 wherein the drilling fluid destination is a shale shaker, and wherein the degasser is further configured to be mounted in association with the shale shaker.

3. The apparatus of claim 2 wherein the container of the drilling fluid destination is a header box of the shale shaker.

4. The apparatus of claim 1 wherein the venturi ejector is operable to:
   receive pressurized motive gas via the first ejector inlet;
   form a vacuum at the second ejector inlet to draw the drilling fluid via the second ejector inlet; and
   discharge a mixture of the motive gas and the drilling fluid via the ejector outlet.

5. The apparatus of claim 1 wherein the degasser further comprises:
   a valve fluidly connected along a first fluid conduit extending between the ejector outlet of the venturi ejector and the separator inlet of the gas-liquid separator, wherein the valve is operable to selectively permit or prevent fluid flow through the first fluid conduit, and wherein in a closed position the valve causes motive gas entering the venturi ejector to be discharged via the second ejector inlet to purge the venturi ejector; and
   a second fluid conduit extending between the second ejector inlet and the container of the drilling fluid destination.

6. The apparatus of claim 1 wherein the degasser further comprises:
   a heater operatively connected between the container of the drilling fluid destination and the gas-liquid separator, wherein the heater is operable to heat the drilling fluid flowing between the container of the drilling fluid destination and the gas-liquid separator.

7. The apparatus of claim 1 further comprising:
   a gas analyzer fluidly connected with the first separator outlet, wherein the gas analyzer is operable to generate signals or information indicative of type and/or quantity of the mud gas released and separated from the drilling fluid.

8. The apparatus of claim 7 further comprising:
   a fluid analyzer fluidly connected with the second separator outlet, wherein the fluid analyzer is operable to generate signals or information indicative of properties and/or characteristics of the degassed drilling fluid.

9. The apparatus of claim 8 further comprising:
   a controller comprising a processor and a memory storing an executable computer program code, wherein the controller is communicatively connected with the gas analyzer and the fluid analyzer and operable to:
      receive the signals or information generated by the gas analyzer and the fluid analyzer; and
      cause wellsite equipment at the oil and gas wellsite to adjust properties of drilling fluid that is to be injected into the wellbore via a drill string during drilling operations based at least partially on the received signals or information.

10. An apparatus comprising:
    a drilling fluid analysis system comprising:
       a gas analyzer;
       a fluid analyzer; and
       a degasser operable to release and separate mud gas entrained in drilling fluid discharged from a wellbore at an oil and gas wellsite, wherein the degasser comprises:
          a gas-liquid separator comprising a fluid separator housing that comprises:
             a separator inlet configured to receive the drilling fluid containing the entrained mud gas;
             a first separator outlet for discharging the mud gas fluidly connected with the gas analyzer; and
             a second separator outlet for discharging degassed drilling fluid fluidly connected with the fluid analyzer, wherein the second separator outlet is configured to be fluidly connected with a drilling fluid destination, wherein the drilling fluid destination comprises a container configured to contain the drilling fluid, and wherein a bottom end of the fluid separator housing is positioned at least partially within the container of the drilling fluid destination such that the second separator outlet is located below a level of the container to which the drilling fluid is filled when contained within the container of the drilling fluid destination.

11. The apparatus of claim 10 wherein the drilling fluid destination is a shale shaker, wherein the container of the drilling fluid destination is a header box of the shale shaker, and wherein the degasser is further configured to be mounted in association with the shale shaker comprising the header box.

12. The apparatus of claim 10 wherein the degasser further comprises:
    a venturi ejector operable to move the drilling fluid containing the entrained mud gas from the container of the drilling fluid destination to the gas-liquid separator, and wherein the venturi ejector comprises:
a first ejector inlet configured to fluidly connect with a motive gas source;
a second ejector inlet configured to fluidly connect with the container of the drilling fluid destination; and
an ejector outlet fluidly connected with the separator inlet.

13. The apparatus of claim 10 wherein the gas analyzer is operable to generate first signals or information indicative of type and/or quantity of the mud gas released and separated from the drilling fluid, and wherein the fluid analyzer is operable to generate second signals or information indicative of properties and/or characteristics of the degassed drilling fluid.

14. The apparatus of claim 13 further comprising a controller comprising:
a processor and a memory storing an executable computer program code, wherein the controller is communicatively connected with the gas analyzer and the fluid analyzer and operable to:
receive the first and second signals or information; and
cause wellsite equipment at the oil and gas wellsite to adjust properties of drilling fluid that is to be injected into the wellbore via a drill string during drilling operations based at least partially on the received first and second signals or information.

15. A method comprising:
performing drilling operations to form a wellbore at an oil and gas wellsite;
operating the degasser of claim 1 at the oil and gas wellsite to release and separate mud gas entrained in drilling fluid discharged from the wellbore;
operating a gas analyzer to analyze the mud gas discharged from the degasser; and
operating a fluid analyzer to analyze degassed drilling fluid discharged from the degasser.

16. The method of claim 15 wherein operating the degasser to release and separate the mud gas entrained in the drilling fluid discharged from the wellbore comprises operating the venturi ejector to move the drilling fluid containing the entrained mud gas from the container of the drilling fluid destination into the gas-liquid separator causing the mud gas and the degassed drilling fluid to be discharged from the gas-liquid separator.

17. The method of claim 15
wherein the drilling fluid destination is a shale shaker, wherein the container of the drilling fluid destination is a header box of the shale shaker, and further comprising:
operating the shale shaker to remove solid particles from the drilling fluid discharged from the wellbore, wherein operating the degasser comprises drawing the drilling fluid from the header box of the shale shaker.

18. The method of claim 15 wherein operating the gas analyzer comprises:
generating first signals or information indicative of type and/or quantity of the mud gas, wherein operating the fluid analyzer comprises generating second signals or information indicative of properties and/or characteristics of the degassed drilling fluid, and wherein the method further comprises:
receiving the first and second signals or information by a processing device; and
operating the processing device to cause wellsite equipment at the oil and gas wellsite to adjust properties of drilling fluid being injected into the wellbore via a drill string during the drilling operations based at least in part on the received first and second signals or information.

* * * * *